(12) United States Patent
Richelson et al.

(10) Patent No.: US 7,214,826 B2
(45) Date of Patent: May 8, 2007

(54) AMINE COMPOUNDS AND INHIBITING NEUROTRANSMITTER REUPTAKE

(75) Inventors: Elliott Richelson, Ponte Vedra Beach, FL (US); Paul R. Carlier, Blacksburg, VA (US)

(73) Assignees: Mayo Foundation for Medical Education and Research, Rochester, MN (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 11/137,313

(22) Filed: May 25, 2005

(65) Prior Publication Data

US 2005/0215647 A1  Sep. 29, 2005

Related U.S. Application Data

(62) Division of application No. 10/755,893, filed on Jan. 12, 2004, now Pat. No. 6,914,080, which is a division of application No. 09/907,377, filed on Jul. 17, 2001, now Pat. No. 6,700,018.

(51) Int. Cl.
  *C07C 215/02* (2006.01)
(52) U.S. Cl. ................. 564/363; 564/355; 514/653
(58) Field of Classification Search ............. 564/349, 564/363, 355; 514/653
  See application file for complete search history.

(56) References Cited

U.S. PATENT DOCUMENTS 6,069,177 A * 5/2000 Carlier et al. ............. 514/652

OTHER PUBLICATIONS

Carlier et al., "*Anti*-Selective Aldol Reaction of Benzylic Nitriles and Synthesis of γ-Amino Alcohols," *J. Org. Chem.*, 1995, 60:7511-7517.

Carlier et al., "Synthesis of a Potent Wide-Spectrum Serotonin-, Norepinephrine-, Dopamine-Reuptake Inhibitor (SNDRI) and a Species-Selective Dopamine-Reuptake Inhibitor Based on the Gamma-Amino Alcohol Functional Group," *Bioorg. Med. Chem. Lett.*, 1998, 8:487-492.

Carlier et al., "HMPA Promotes Retro-Aldol Reaction, Resulting in Syn-Selective Addition of Lithiated 1-Naphthylacetonitrile to Aromatic Aldehdes," *Org. Lett.*, 2000, 2(16):2443-2445.

Lowry et al., "Protein Measurement with the Folin Phenol Reagent," *J. Biol. Chem.*, 1951, 193:265-275.

Munson and Rodbard, "LIGAND: A Versatile Computerized Approach for Characterization of Ligand-Binding Systems," *Analyt. Biochem.*, 1980, 107:220-239.

Pacholczyk et al., "Expression cloning of a cocaine-and antidepressant-sensitive human noradrenaline transporter," *Nature*, 1991, 350:350-354.

Pfenning and Richelson, "Methods for Studying Receptors with Cultured Cells of Nervous Tissue Origin," *Methods in Neurotransmitter Receptor Analysis*, 1990, Raven Press, New York, pp. 147-175.

Pristupa et al., "Pharmacological Heterogeneity of the Cloned and Native Human Dopamine Transporter: Disassociation of [$^3$H]WIN 35,428 and [$^3$H]GBR 12,935 Binding," *Mol. Pharmacol.*, 1994, 45:125-135.

Ramamoorthy et al., "Antidepressant- and cocaine-sensitive human serotonin transporter: Molecular cloning, expression, and chromosomal localization," *Proc. Natl. Acad. Sci. USA*, 1993, 90:2542-2546.

Tatsumi et al., "Pharmacological profile of antidepressants and related compounds at human monoamine transporters," *Eur. J. Pharmacol.*, 1997, 340:249-258.

\* cited by examiner

*Primary Examiner*—Samuel Barts
(74) *Attorney, Agent, or Firm*—Fish & Richardson P.C.

(57) ABSTRACT

The invention relates to amine compounds as well as methods and materials involved in modulating neurotransmitter reuptake. Specifically, the invention provides amine compounds, methods for synthesizing amine compounds, and methods for inhibiting neurotransmitter reuptake.

5 Claims, 7 Drawing Sheets

FIGURE 1

N-methyl-3-hydroxy-2-(2'-naphthyl)-3-phenylpropylamine

(2R,3R)-N-methyl-3-hydroxy-2-(2'-naphthyl)-3-phenylpropylamine (2S,3R)-N-methyl-3-hydroxy-2-(2'-naphthyl)-3-phenylpropylamine (2S,3S)-N-methyl-3-hydroxy-2-(2'-naphthyl)-3-phenylpropylamine (2R,3S)-N-methyl-3-hydroxy-2-(2'-naphthyl)-3-phenylpropylamine

FIGURE 2

N-methyl-3-hydroxy-4,4-dimethyl2-(2'-naphthyl)pentylamine

(2R,3R)-N-methyl-3-hydroxy-4,4-dimethyl-2-(2'-naphthyl)pentylamine (2S,3R)-N-methyl-3-hydroxy-4,4-dimethyl-2-(2'-naphthyl)pentylamine (2S,3S)-N-methyl-3-hydroxy-4,4-dimethyl-2-(2'-naphthyl)pentylamine (2R,3S)-N-methyl-3-hydroxy-4,4-dimethyl-2-(2'-naphthyl)pentylamine

FIGURE 3

3-hydroxy-4-methyl-2-(2'-naphthyl)pentylamine

(2R,3S)-3-hydroxy-4-methyl-2-
(2'-naphthyl)pentylamine (2S,3S)-3-hydroxy-4-methyl-2-(2'-
naphthyl)pentylamine (2S,3R)-3-hydroxy-4-methyl-2-
(2'-naphthyl)pentylamine (2R,3R)-3-hydroxy-4-methyl-2-(2'
-naphthyl)pentylamine

FIGURE 4

*N,N*-dimethyl-3-hydroxy-4-methyl-2-(2'-naphthyl)pentylamine

(2*R*,3*S*)-*N,N*-dimethyl-3-hydroxy-4-methyl-2-(2'-naphthyl)pentylamine (2*S*,3*S*)-*N,N*-dimethyl-3-hydroxy-4-methyl-2-(2'-naphthyl)pentylamine (2*S*,3*R*)-*N,N*-dimethyl-3-hydroxy-4-methyl-2-(2'-naphthyl)pentylamine (2*R*,3*R*)-*N,N*-dimethyl-3-hydroxy-4-methyl-2-(2'-naphthyl)pentylamine

FIGURE 5

*N*-methyl-3-hydroxy-4-methyl-2-(2'-naphthyl)pentylamine

(2*R*,3*S*)-*N*-methyl-3-hydroxy-4-methyl-2-(2'-naphthyl)pentylamine (2*S*,3*S*)-*N*-methyl-3-hydroxy-4-methyl-2-(2'-naphthyl)pentylamine (2*S*,3*R*)-*N*-methyl-3-hydroxy-4-methyl-2-(2'-naphthyl)pentylamine (2*R*,3*R*)-*N*-methyl-3-hydroxy-4-methyl-2-(2'-naphthyl)pentylamine

FIGURE 6

(2S,3R)-3-hydroxy-2-(2'-naphthyl)-3-phenylpropylamine (2R,3S)-3-hydroxy-2-(2'-naphthyl)-3-phenylpropylamine

FIGURE 7

(2S,3R)-N,N-dimethyl-3-hydroxy-2-(2'-naphthyl)-3-phenylpropylamine (2R,3S)-N,N-dimethyl-3-hydroxy-2-(2'-naphthyl)-3-phenylpropylamine

AMINE COMPOUNDS AND INHIBITING NEUROTRANSMITTER REUPTAKE

CROSS-REFERENCE TO RELATED APPLICATIONS

This application is a divisional of U.S. application Ser. No. 10/755,893, filed Jan. 12, 2004, now U.S. Pat. No. 6,914,080 which is a divisional of U.S. application Ser. No. 09/907,377, filed Jul. 17, 2001 now U.S. Pat. No. 6,700,018. The disclosure of the prior applications are considered part of (and are incorporated by reference in) the disclosure of this application.

BACKGROUND

1. Technical Field

The invention relates to amine compounds as well as methods and materials involved in modulating neurotransmitter reuptake.

2. Background Information

Neuronal signals are transmitted from cell to cell at specialized sites of contact known as synapses. The usual mechanism of transmission is indirect. The cells are electrically isolated from one another, the presynaptic cell being separated from the postsynaptic cell by a narrow synaptic cleft. A change of electrical potential in the presynaptic cell triggers it to release signaling molecules known as neurotransmitters. The neurotransmitters rapidly diffuse across the synaptic cleft and provoke an electrical change in the postsynaptic cell by binding to neurotransmitter-gated ion channels. After release, the excess neurotransmitters are rapidly removed, either by specific enzymes in the synaptic cleft or by reuptake into the presynaptic cell or surrounding glial cells. Reuptake is mediated by a variety of neurotransmitter transporters. Rapid removal ensures both spatial and temporal precision of signaling at a synapse. For example, rapid reuptake can prevent excess neurotransmitters from influencing neighboring cells and can clear the synaptic cleft before the next pulse of neurotransmitter release so that the timing of repeated, rapid signaling events is accurately communicated to the postsynaptic cell.

An imbalance of neurotransmitters in the brain can occur when not enough neurotransmitter is made and released from presynaptic cells or the reuptake of neurotransmitters by presynaptic cells is too rapid. If neurotransmitters such as serotonin, norepinephrine, or dopamine are not made and released in effective amounts or are cleared from the synaptic cleft too quickly, then cell-to-cell communication can be affected. Clinical manifestations of such imbalances include depression and related anxiety disorders. Serotonin-, norepinephrine-, dopamine-reuptake inhibitors (SNDRIs) represent a class of potent, wide-spectrum antidepressant medications that inhibit the reuptake of these neurotransmitters back into presynaptic cells. Inhibiting neurotransmitter reuptake can increase the amount of neurotransmitter present in the synapse, thus helping to normalize the transmission of neuronal signals and alleviate the symptoms of depression and related anxiety disorders.

SUMMARY

The invention relates to amine compounds as well as methods and materials involved in modulating neurotransmitter reuptake. Specifically, the invention provides amine compounds, methods for synthesizing amine compounds, and methods for inhibiting neurotransmitter reuptake. The amine compounds provided herein can be used as potent, wide-spectrum antidepressant medications for inhibiting neurotransmitter reuptake and treating anxiety disorders. In addition, the methods provided herein for synthesizing amine compounds allow for synthesis in a reliable and efficient manner.

In general, the invention features a composition containing N-methyl-3-hydroxy-2-(2'-naphthyl)-3-phenylpropylamine. The N-methyl-3-hydroxy-2-(2'-naphthyl)-3-phenylpropylamine can contain (2R, 3R)-N-methyl-3-hydroxy-2-(2'-naphthyl)-3-phenylpropylamine or (2S, 3S)-N-methyl-3-hydroxy-2-(2'-naphthyl)-3-phenylpropylamine. The N-methyl-3-hydroxy-2-(2'-naphthyl)-3-phenylpropylamine can contain (2R, 3S)-N-methyl-3-hydroxy-2-(2'-naphthyl)-3-phenylpropylamine or (2S, 3R)-N-methyl 3-hydroxy-2-(2'-naphthyl)-3-phenylpropylamine. The N-methyl-3-hydroxy-2-(2'-naphthyl)-3-phenylpropylamine can contain (a) two compounds selected from the following group: (2R, 3R)-N-methyl-3-hydroxy-2-(2'-naphthyl)-3-phenylpropylamine, (2S, 3S)-N-methyl-3-hydroxy-2-(2'-naphthyl)-3-phenylpropylamine, (2R, 3S)-N-methyl-3-hydroxy-2-(2'-naphthyl)-3-phenylpropylamine, and (2S, 3R)-N-methyl-3-hydroxy-2-(2'-naphthyl)-3-phenylpropylamine; (b) three compounds selected from the following group: (2R, 3R)-N-methyl-3-hydroxy-2-(2'-naphthyl)-3-phenylpropylamine, (2S, 3S)-N-methyl-3-hydroxy-2-(2'-naphthyl)-3-phenylpropylamine, (2R, 3S)-N-methyl-3-hydroxy-2-(2'-naphthyl)-3-phenylpropylamine, and (2S, 3R)-N-methyl-3-hydroxy-2-(2'-naphthyl)-3-phenylpropylamine; or (c) (2R, 3R)-N-methyl-3-hydroxy-2-(2'-naphthyl)-3-phenylpropylamine, (2S, 3 S)-N-methyl-3-hydroxy-2-(2'-naphthyl)-3-phenylpropylamine, (2R, 3S)-N-methyl-3-hydroxy-2-(2'-naphthyl)-3-phenylpropylamine, and (2S, 3R)-N-methyl-3-hydroxy-2-(2'-naphthyl)-3-phenylpropylamine. The composition can contain a pharmaceutically acceptable carrier. At least about 35 percent of the composition (e.g., at least about 40, 45, 50, 55, 60, 65, 70, 75, 80, 85, 90, 95, or 99 percent of the composition) can be the N-methyl-3-hydroxy-2-(2'-naphthyl)-3-phenylpropylamine.

In another embodiment, the invention features a composition containing N-methyl-3-hydroxy-4,4-dimethyl-2-(2'-naphthyl)pentylamine. The N-methyl-3-hydroxy-4,4-dimethyl-2-(2'-naphthyl)pentylamine can contain (2R, 3R)-N-methyl-3-hydroxy-4,4-dimethyl-2-(2'-naphthyl) pentylamine or (2S, 3S)-N-methyl-3-hydroxy-4,4-dimethyl-2-(2'-naphthyl)pentylamine. The N-methyl-3-hydroxy-4,4-dimethyl-2-(2'-naphthyl)pentylamine can contain (2R, 3S)-N-methyl-3-hydroxy-4,4-dimethyl-2-(2'-naphthyl) pentylamine or (2S, 3R)-N-methyl-3-hydroxy-4,4-dimethyl-2-(2'-naphthyl)pentylamine. The N-methyl-3-hydroxy-4,4-dimethyl-2-(2'-naphthyl)pentylamine can contain (a) two of the compounds selected from the following group: (2R, 3R)-N-methyl-3-hydroxy-4,4-dimethyl-2-(2'-naphthyl)pentylamine, (2S, 3S)-N-methyl-3-hydroxy-4,4-dimethyl-2-(2'-naphthyl)pentylamine, (2R, 3S)-N-methyl-3-hydroxy-4,4-dimethyl-2-(2'-naphthyl)pentylamine, and (2S, 3R)-N-methyl-3-hydroxy-4,4-dimethyl-2-(2'-naphthyl) pentylamine; (b) three of the compounds selected from the following group: (2R, 3R)-N-methyl-3-hydroxy-4,4-dimethyl-2-(2'-naphthyl)pentylamine, (2S, 3S)-N-methyl-3-hydroxy-4,4-dimethyl-2-(2'-naphthyl)pentylamine, (2R, 3S)-N-methyl-3-hydroxy-4,4-dimethyl-2-(2'-naphthyl) pentylamine, and (2S, 3R)-N-methyl-3-hydroxy-4,4-dimethyl-2-(2'-naphthyl)pentylamine; or (c) (2R, 3R)-N-methyl-3-hydroxy-4,4-dimethyl-2-(2'-naphthyl) pentylamine, (2S, 3S)-N-methyl-3-hydroxy-4,4-dimethyl-2-(2'-naphthyl)pentylamine, (2R, 3S)-N-methyl-3-hydroxy-4, 4-dimethyl-2-(2'-naphthyl)pentylamine, and (2S, 3R)-N-methyl-3-hydroxy-4,4-dimethyl-2-(2'-naphthyl)pentylamine. The composition can contain a pharmaceutically acceptable carrier. At least about 35 percent of the composition (e.g., at least about 40, 45, 50, 55, 60, 65, 70, 75, 80, 85, 90, 95, or 99 percent of the composition) can be the N-methyl-3-hydroxy-4,4-dimethyl-2-(2'-naphthyl)pentylamine.

Another embodiment of the invention features a composition containing 3-hydroxy-4-methyl-2-(2'-naphthyl)pentylamine. The 3-hydroxy-4-methyl-2-(2'-naphthyl)pentylamine can contain (2R, 3R)-3-hydroxy-4-methyl-2-(2'-naphthyl)pentylamine or (2S, 3S)-3-hydroxy-4-methyl-2-(2'-naphthyl)pentylamine. The 3-hydroxy-4-methyl-2-(2'-naphthyl)pentylamine can contain (2R, 3S)-3-hydroxy-4-methyl-2-(2'-naphthyl)pentylamine or (2S, 3R)-3-hydroxy-4-methyl-2-(2'-naphthyl)pentylamine. The 3-hydroxy-4-methyl-2-(2'-naphthyl)pentylamine can contain (a) two compounds selected from the following group: (2R, 3R)-3-hydroxy-4-methyl-2-(2'-naphthyl)pentylamine, (2S, 3S)-3-hydroxy-4-methyl-2-(2'-naphthyl)pentylamine, (2R, 3S)-3-hydroxy-4-methyl-2-(2'-naphthyl)pentylamine, and (2S, 3R)-3-hydroxy-4-methyl-2-(2'-naphthyl)pentylamine; (b) three compounds selected from the following group: (2R, 3R)-3-hydroxy-4-methyl-2-(2'-naphthyl)pentylamine, (2S, 3S)-3-hydroxy-4-methyl-2-(2'-naphthyl)pentylamine, (2R, 3S)-3-hydroxy-4-methyl-2-(2'-napthyl)pentylamine, and (2S, 3R)-3-hydroxy-4-methyl-2-(2'-naphthyl)pentylamine; or (c) (2R, 3R)-3-hydroxy 4-methyl-2-(2'-naphthyl)pentylamine, (2S, 3S)-3-hydroxy-4-methyl-2-(2'-naphthyl)pentylamine, (2R, 3S)-3-hydroxy-4-methyl-2-(2'-naphthyl)pentylamine, and (2S, 3R)-3-hydroxy-4-methyl-2-(2'-naphthyl)pentylamine. The composition can contain a pharmaceutically acceptable carrier. At least about 35 percent of the composition (e.g., at least about 40, 45, 50, 55, 60, 65, 70, 75, 80, 85, 90, 95, or 99 percent of the composition) can be the 3-hydroxy-4-methyl-2-(2'-naphthyl)pentylamine.

Another embodiment of the invention features a composition containing N,N-dimethyl-3-hydroxy-4-methyl-2-(2'-naphthyl)pentylamine. The N,N-dimethyl-3-hydroxy-4-methyl-2-(2'-naphthyl)pentylamine can contain (2R, 3R)-N,N-dimethyl-3-hydroxy-4-methyl-2-(2'-naphthyl)pentylamine or (2S, 3S)-N,N-dimethyl-3-hydroxy-4-methyl-2-(2'-naphthyl)pentylamine. The N,N-dimethyl-3-hydroxy-4-methyl-2-(2'-naphthyl)pentylamine can contain (2R, 3S)-N,N-dimethyl-3-hydroxy-4-methyl-2-(2'-naphthyl)pentylamine or (2S, 3R)-N,N-dimethyl-3-hydroxy-4-methyl-2-(2'-naphthyl)pentylamine. The N,N-dimethyl-3-hydroxy-4-methyl-2-(2'-naphthyl)pentylamine can contain (a) two compounds selected from the following group: (2R, 3R)-N,N-dimethyl-3-hydroxy-4-methyl-2-(2'-naphthyl)pentylamine, (2S, 3S)-N,N-dimethyl-3-hydroxy-4-methyl-2-(2'-naphthyl)pentylamine, (2R, 3S)-N,N-dimethyl-3-hydroxy -4-methyl-2-(2'-naphthyl)pentylamine, and (2S, 3R)-N,N-dimethyl-3-hydroxy-4-methyl-2-(2'-naphthyl)pentylamine; (b) three compounds selected from the following group: (2R, 3R)-N,N-dimethyl-3-hydroxy-4-methyl-2-(2'-naphthyl)pentylamine, (2S, 3S)-N,N-dimethyl-3-hydroxy-4-methyl-2-(2'-naphthyl)pentylamine, (2R, 3S)-N,N-dimethyl-3-hydroxy-4-methyl-2-(2'-naphthyl)pentylamine, and (2S, 3R)-N,N-dimethyl-3-hydroxy-4-methyl-2-(2'-naphthyl)pentylamine; or (c) (2R, 3R)-N,N-dimethyl-3-hydroxy-4-methyl-2-(2'-naphthyl)pentylamine, (2S, 3S)-N,N-dimethyl-3-hydroxy-4-methyl-2-(2'-naphthyl)pentylamine, (2R, 3S)-N,N-dimethyl-3-hydroxy-4-methyl-2-(2'-naphthyl)pentylamine and (2S, 3R)-N,N-dimethyl-3-hydroxy-4-methyl-2-(2'-naphthyl)pentylamine. The composition can contain a pharmaceutically acceptable carrier. At least about 35 percent of the composition (e.g., at least about 40, 45, 50, 55, 60, 65, 70, 75, 80, 85, 90, 95, or 99 percent of the composition) can be the N,N-dimethyl-3-hydroxy-4-methyl-2-(2'-naphthyl)pentylamine.

Another embodiment of the invention features a composition containing N-methyl-3-hydroxy-4-methyl-2-(2'-naphthyl)pentylamine. The N-methyl-3-hydroxy-4-methyl-2-(2'-naphthyl)pentylamine can contain (2R, 3R)-N-methyl-3-hydroxy-4-methyl-2-(2'-naphthyl)pentylamine or (2S, 3S)-N-methyl-3-hydroxy-4-methyl-2-(2'-naphthyl)pentylamine The N-methyl-3-hydroxy-4-methyl-2-(2'-naphthyl)pentylamine can contain (2R, 3S)-N-methyl-3-hydroxy-4-methyl-2-(2'-naphthyl)pentylamine or (2S, 3R)-N-methyl-3-hydroxy-4-methyl-2-(2'-naphthyl)pentylamine. The N-methyl-3-hydroxy-4-methyl-2-(2'-naphthyl)pentylamine can contain (a) two compounds selected from the following group: (2R, 3R)-N-methyl-3-hydroxy-4-methyl-2-(2'-naphthyl)pentylamine, (2S, 3S)-N-methyl-3-hydroxy-4-methyl-2-(2'-naphthyl)pentylamine, (2R, 3S)-N-methyl-3-hydroxy-4-methyl-2-(2'-naphthyl)pentylamine, and (2S, 3R)-N-methyl-3-hydroxy-4-methyl-2-(2'-naphthyl)pentylamine;

(b) three compounds selected from the following group: (2R, 3R)-N-methyl-3-hydroxy-4-methyl-2-(2'-naphthyl)pentylamine, (2S, 3S)-N-methyl-3-hydroxy-4-methyl-2-(2'-naphthyl)pentylamine, (2R, 3S)-N-methyl-3-hydroxy-4-methyl-2-(2'-naphthyl)pentylamine, and (2S, 3R)-N-methyl-3-hydroxy-4-methyl-2-(2'-naphthyl)pentylamine; or (c) (2R, 3R)-N-methyl-3-hydroxy-4-methyl-2-(2'-naphthyl)pentylamine, (2S, 3 S)-N-methyl-3-hydroxy-4-methyl-2-(2'-naphthyl)pentylamine, (2R, 3S)-N-methyl-3-hydroxy-4-methyl-2-(2'-naphthyl)pentylamine, and (2S, 3R)-N-methyl-3-hydroxy-4-methyl-2-(2'-naphthyl)pentylamine. The composition can contain a pharmaceutically acceptable carrier. At least about 35 percent of the composition (e.g., at least about 40, 45, 50, 55, 60, 65, 70, 75, 80, 85, 90, 95, or 99 percent of the composition) can be the N-methyl-3-hydroxy-4-methyl-2-(2'-naphthyl)pentylamine.

Another embodiment of the invention features a composition containing 3-hydroxy-2-(2'-naphthyl)-3-phenylpropylamine with the 3-hydroxy-2-(2'-naphthyl)-3-phenylpropylamine being (2R, 3S)-3-hydroxy-2-(2'-naphthyl)-3-phenylpropylamine or (2S, 3R)-3-hydroxy-2-(2'-naphthyl)-3-phenylpropylamine. The 3-hydroxy-2-(2'-naphthyl)-3-phenylpropylamine can be (2R, 3S)-3-hydroxy-2-(2'-naphthyl)-3-phenylpropylamine. The 3-hydroxy-2-(2'-naphthyl)-3-phenylpropylamine can be (2S, 3R)-3-hydroxy-2-(2'-naphthyl)-3-phenylpropylamine. The composition can lack (2R, 3R)-3-hydroxy-2-(2'-naphthyl)-3-phenylpropylamine and (2S, 3S)-3-hydroxy-2-(2'naphthyl)-3-phenylpropylamine. The composition can contain a pharmaceutically acceptable carrier. At least about 35 percent of the composition (e.g., at least about 40, 45, 50, 55, 60, 65, 70, 75, 80, 85, 90, 95, or 99 percent of the composition) can be the 3-hydroxy-2-(2'-naphthyl)-3 -phenylpropylamine.

Another embodiment of the invention features a composition containing N,N-dimethyl-3-hydroxy-2-(2'-naphthyl)-3-phenylpropylamine with the N,N-dimethyl-3-hydroxy-2-(2'-naphthyl)-3-phenylpropylamine being (2R, 3S)-N,N-dimethyl-3-hydroxy-2-(2'-naphthyl)-3-phenylpropylamine or (2S, 3R)-N,N-dimethyl-3-hydroxy-2-(2'-naphthyl)-3-phenylpropylamine. The N,N-dimethyl-3-hydroxy-2-(2'-naphthyl)-3-phenylpropylamine can be (2R, 3S)-N,N-dimethyl-3-hydroxy-2-(2'-naphthyl)-3-phenylpropylamine. The N,N-dimethyl-3-hydroxy-2-(2'-naphthyl)-3-phenylpropylamine can be (2S, 3R)-N,N-dimethyl-3-hydroxy-2-(2'- naphthyl)-3-phenylpropylamine. The composition can lack (2R, 3R)-N,N-dimethyl-3-hydroxy-2-(2'-naphthyl)-3-phenylpropylamine and (2S, 3S)-N,N-dimethyl-3-hydroxy-2-(2'-naphthyl)-3-phenylpropylamine. The composition can contain a pharmaceutically acceptable carrier. At least about 35 percent of the composition (e.g., at least about 40, 45, 50, 55, 60, 65, 70, 75, 80, 85, 90, 95, or 99 percent of the composition) can be the N,N-dimethyl-3-hydroxy-2-(2'-naphthyl)-3-phenylpropylamine.

In another aspect, the invention features a method for inhibiting neurotransmitter reuptake in a mammal (e.g., human). The method includes administering a composition containing at least one compound to the mammal, wherein the composition contains at least one compound selected from the following group: N-methyl-3-hydroxy-2-(2'-naphthyl)-3-phenylpropylamine, N-methyl-3-hydroxy-4,4-dimethyl-2-(2'-naphthyl)pentylamine, 3-hydroxy-4-methyl-2-(2'-naphthyl)pentylamine, N,N-dimethyl-3-hydroxy-4-methyl-2-(2'-naphthyl)pentylamine, N-methyl-3-hydroxy-4-methyl-2-(2'-naphthyl)pentylamine, (2R, 3S)-3-hydroxy-2-(2'-naphthyl)-3-phenylpropylamine, (2S, 3R)-3-hydroxy-2-(2'-naphthyl)-3-phenylpropylamine, (2R, 3S)-N,N-dimethyl-3-hydroxy-2-(2'-naphthyl)-3-phenylpropylamine, and (2S, 3R)-N,N-dimethyl-3-hydroxy-2-(2'-naphthyl)-3-phenylpropylamine. The neurotransmitter reuptake can be norepinephrine or epinephrine reuptake. The neurotransmitter reuptake can be dopamine reuptake or serotonin reuptake. At least about 35 percent of the composition (e.g., at least about 40, 45, 50, 55, 60, 65, 70, 75, 80, 85, 90, 95, or 99 percent of the composition) can be the compound.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
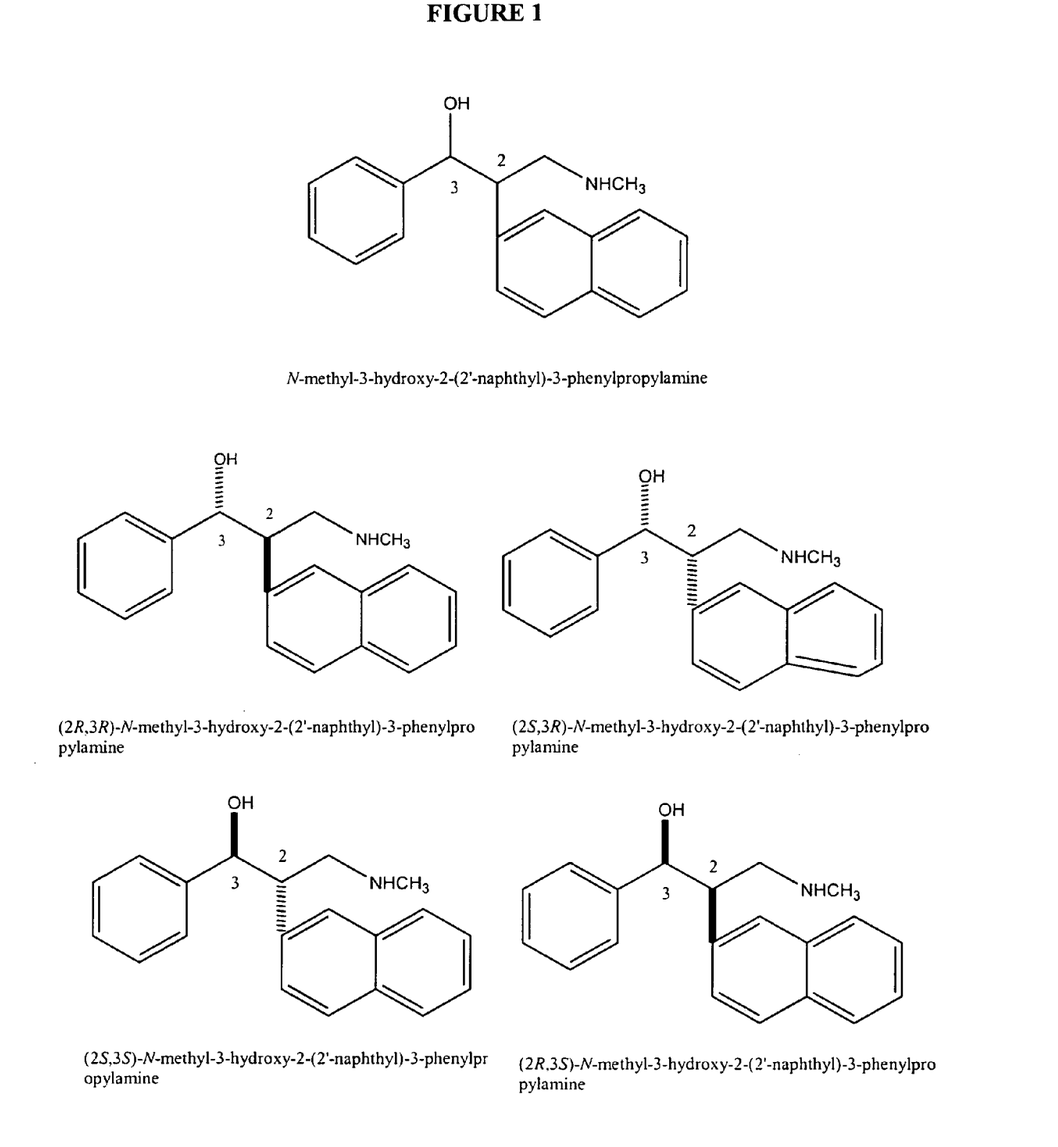
FIG. 1 is a diagram of N-methyl-3-hydroxy-2-(2'-naphthyl)-3-phenylpropylamine and its four stereoisomers.
Figure 2:
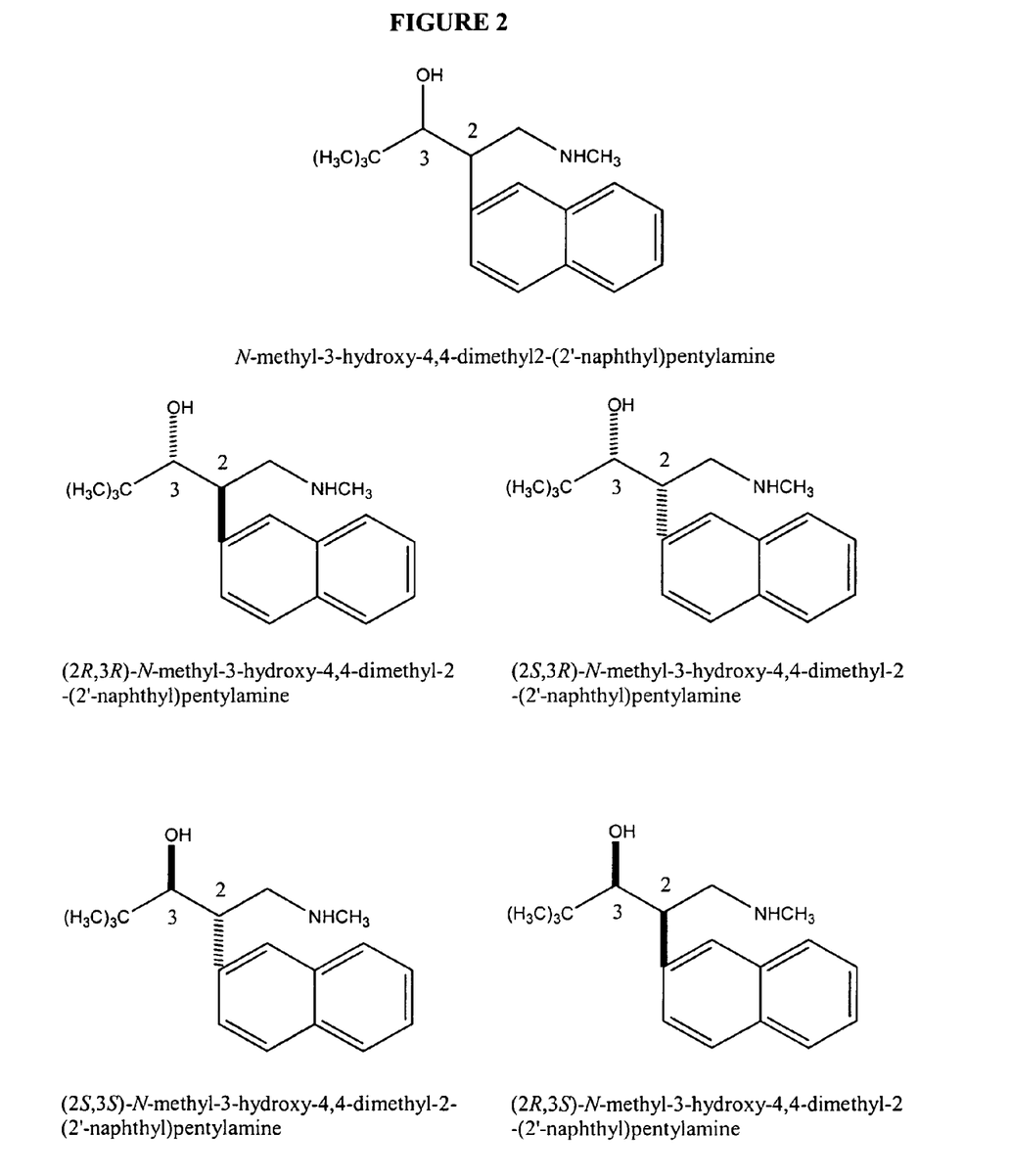
FIG. 2 is a diagram of N-methyl-3-hydroxy-4,4-dimethyl-2-(2' naphthyl) pentylamine and its four stereoisomers.
Figure 3:
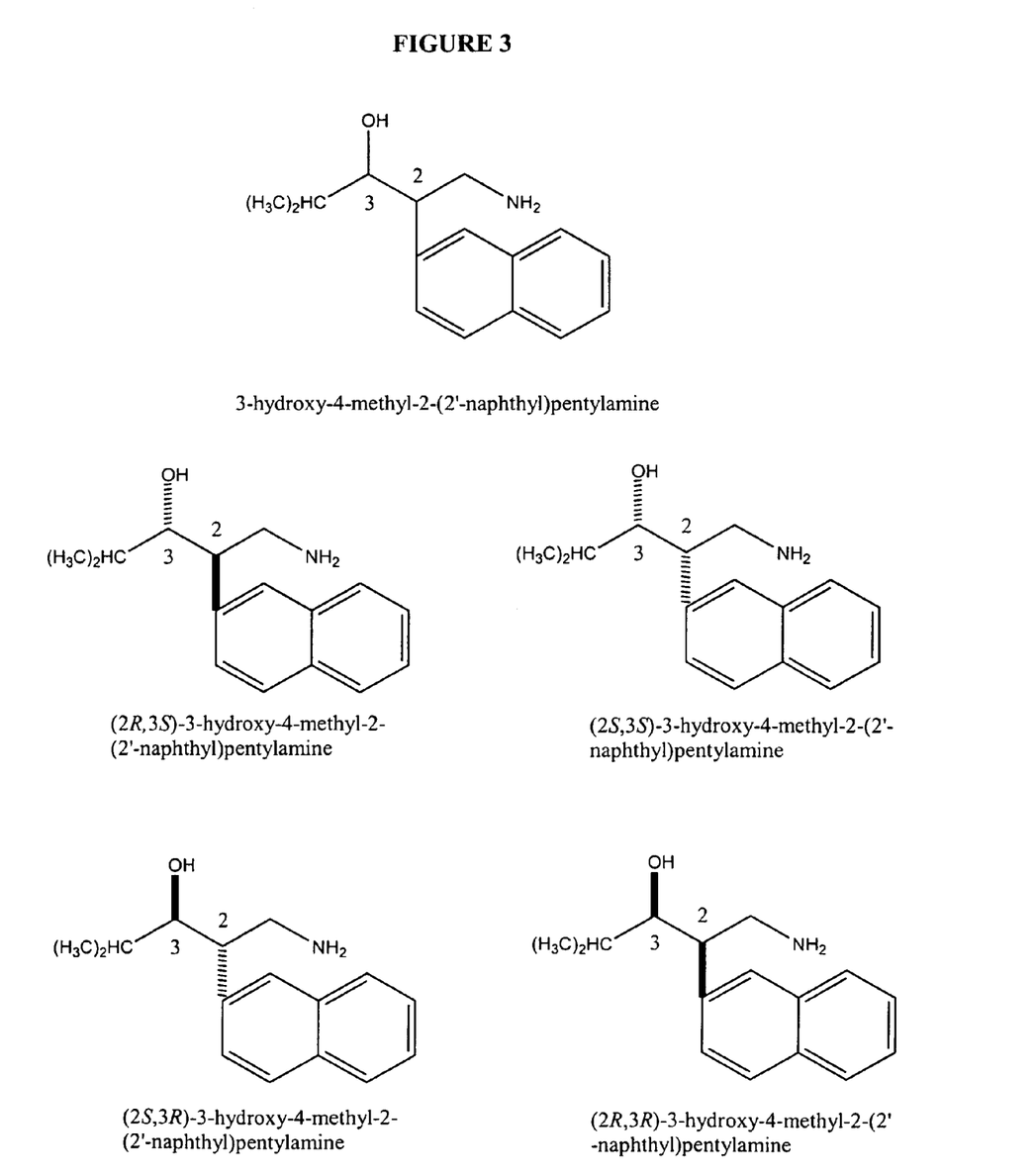
FIG. 3 is a diagram of 3-hydroxy-4-methyl-2-(2'-naphthyl) pentylamine and its four stereoisomers.
Figure 4:
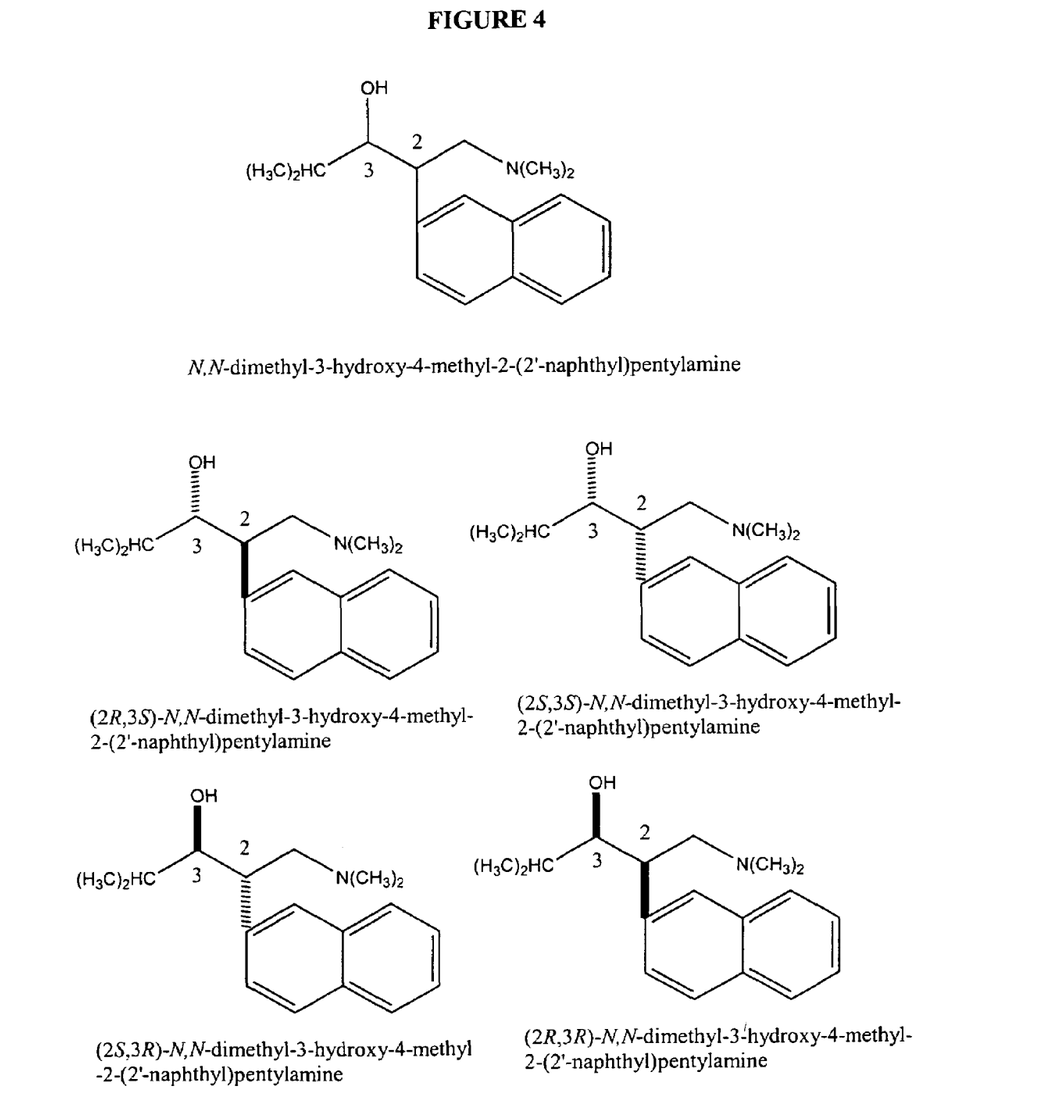
FIG. 4 is a diagram of N,N-dimethyl-3-hydroxy-4-methyl-2-(2'-naphthyl) pentylamine and its four stereoisomers.
Figure 5:
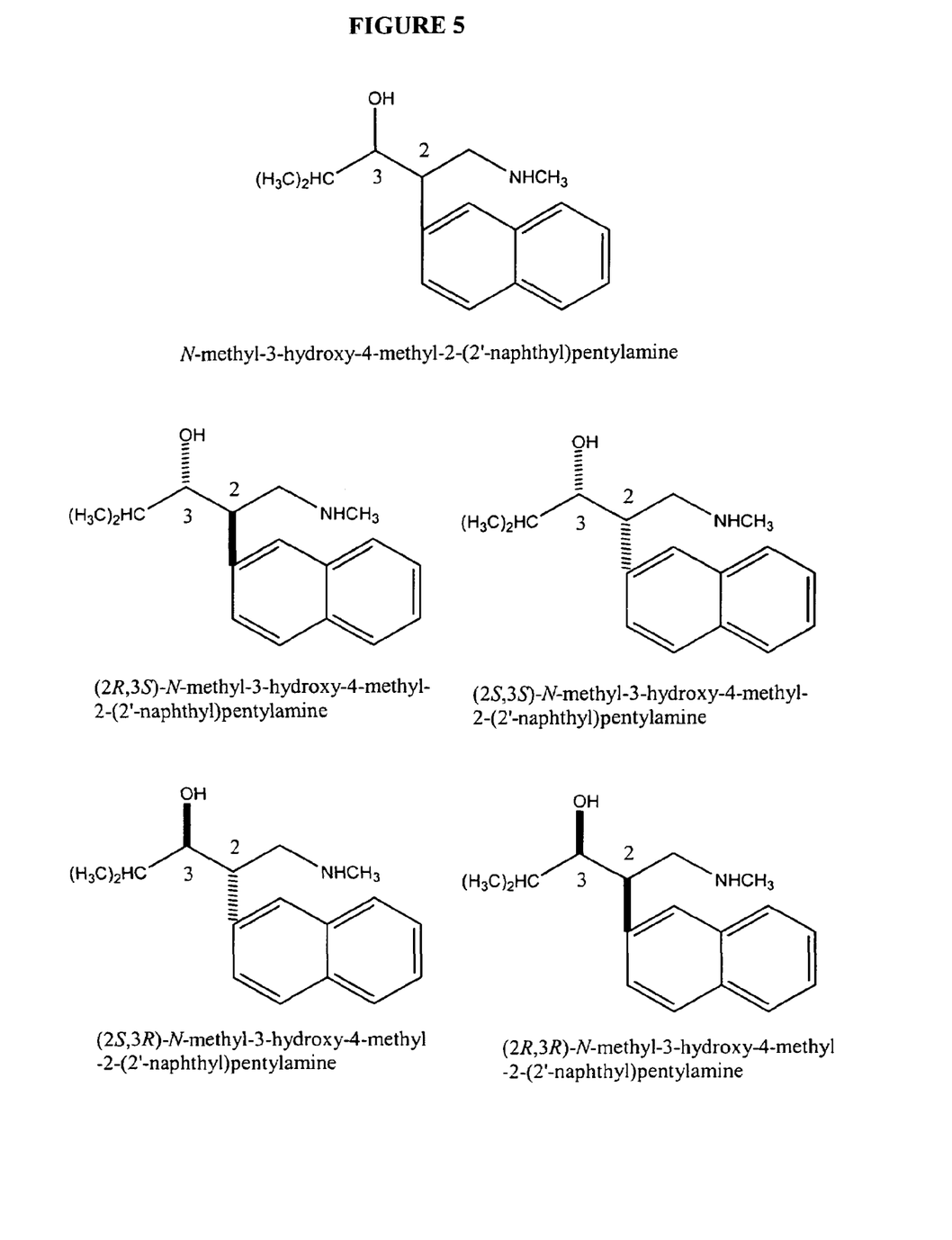
FIG. 5 is a diagram of N-methyl-3-hydroxy-4-methyl-2-(2'-naphthyl) pentylamine and its four stereoisomers.
Figure 6:
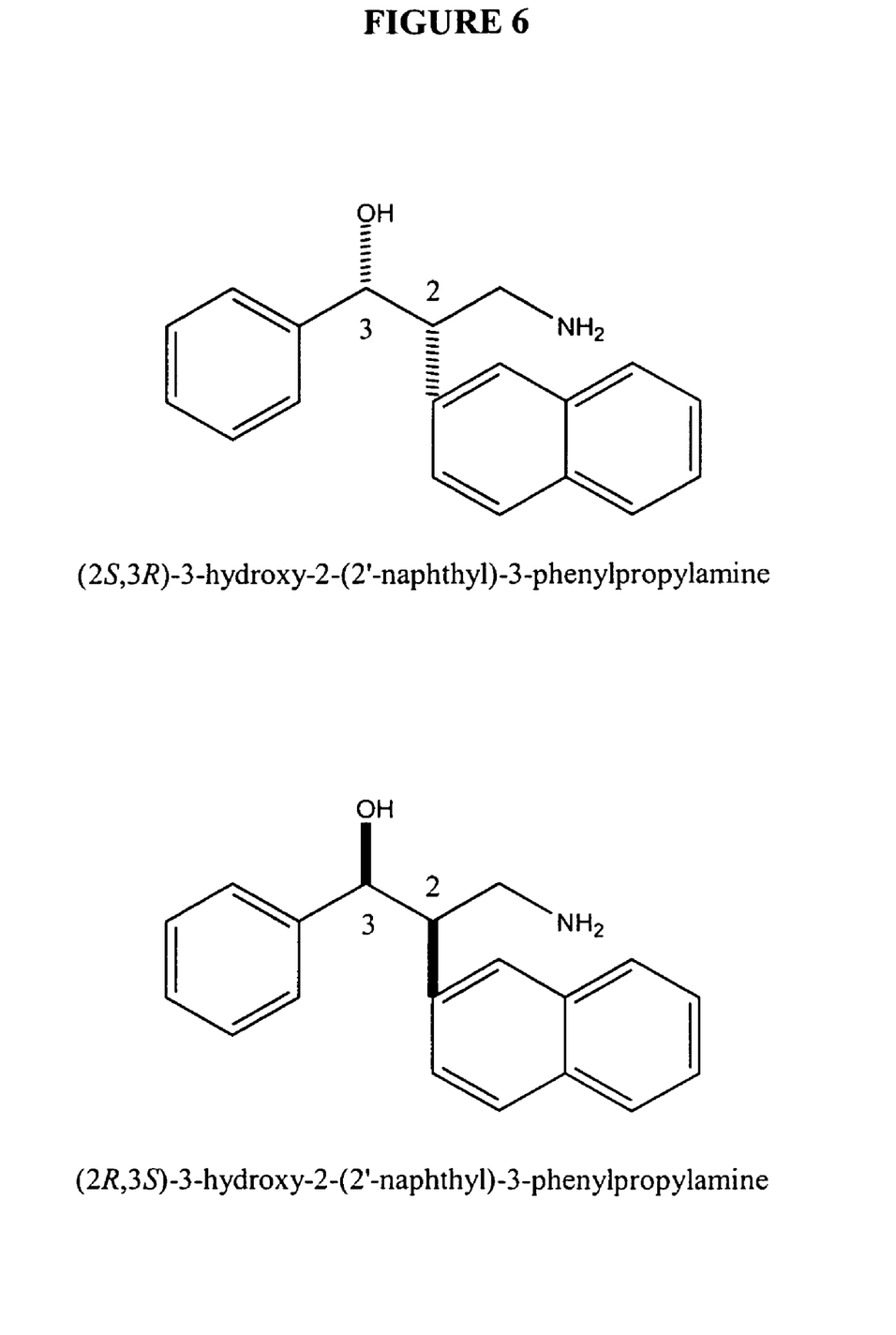
FIG. 6 is a diagram of (2S, 3R)-3-hydroxy-2-(2'-naphthyl)-3-phenylpropylamine and (2R, 3s)-3-hydroxy-2-(2'-naphthyl)-3-phenylpropylamine.
Figure 7:
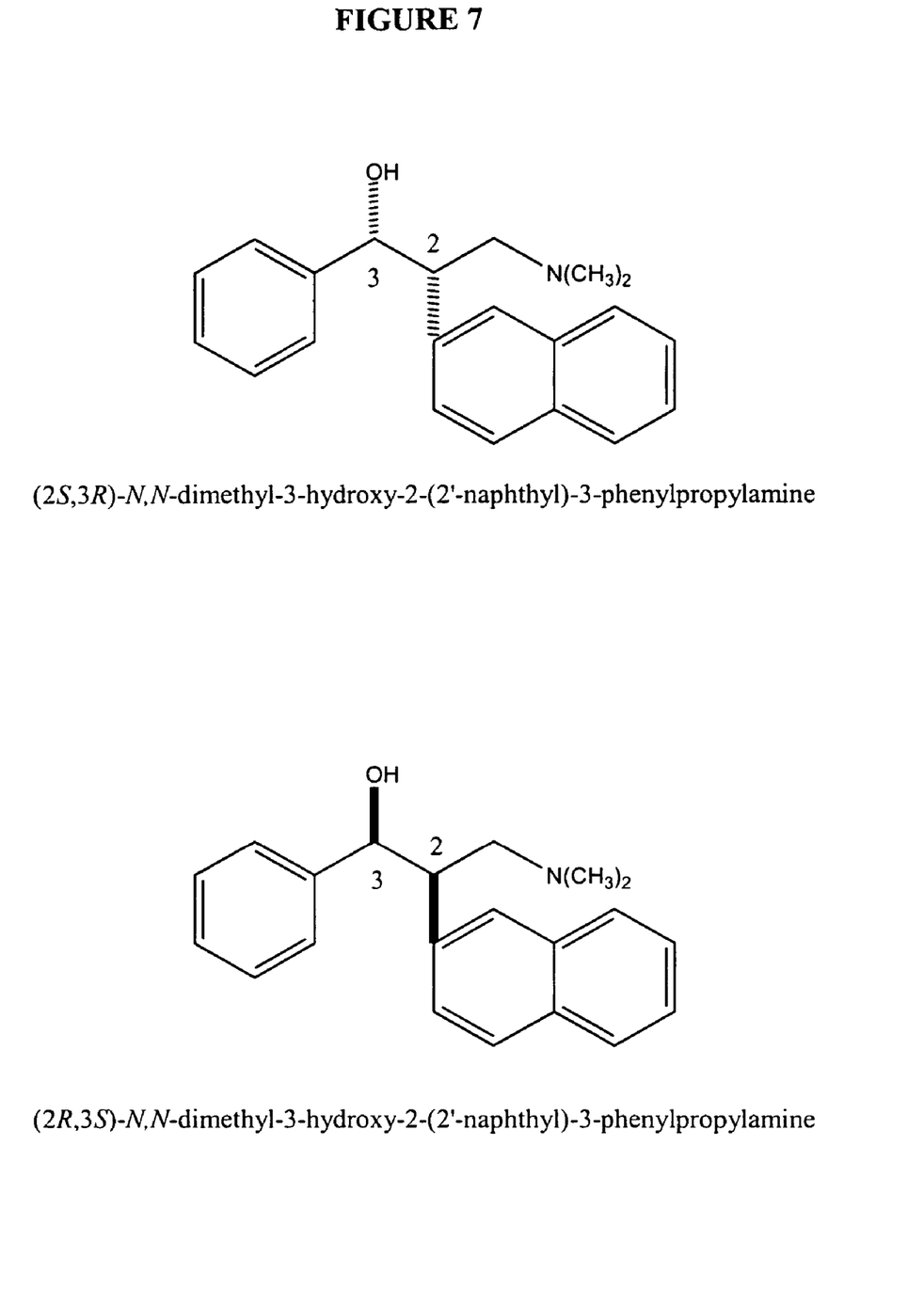
FIG. 7 is a diagram of (2S, 3R)-N,N-dimethyl-3-hydroxy-2-(2'-naphthyl)-3-phenylpropylamine and (2R, 3S)-N,N-dimethyl-3-hydroxy-2-(2'-naphthyl)-3-phenylpropylamine.

The invention relates to amine compounds as well as methods and materials involved in modulating neurotransmitter reuptake. Specifically, the invention provides amine compounds such as 3-hydroxy-pentylamine and 3-hydroxy-propylamine compounds, methods for synthesizing amine compounds, and methods for inhibiting neurotransmitter reuptake. For example, the invention provides N-methyl-3-hydroxy-2-(2'-naphthyl)-3-phenylpropylamine, N-methyl-3-hydroxy-4,4-dimethyl-2-(2'-naphthyl)pentylamine, 3-hydroxy-4-methyl-2-(2'-naphthyl)pentylamine, N,N-dimethyl-3-hydroxy-4-methyl-2-(2'-naphthyl)pentylamine, N-methyl-3-hydroxy-4-methyl-2-(2'-naphthyl)pentylamine, 3-hydroxy-2-(2'-naphthyl)-3-phenylpropylamine, and N,N-dimethyl-3-hydroxy-2-(2'-naphthyl)-3-phenylpropylamine compounds. It is understood that a particular 3-hydroxy-pentylamine or 3-hydroxy-propylamine compound includes any one of that compound's stereoisomers as well as any combination thereof. For example, an N-methyl-3-hydroxy-2-(2'-naphthyl)-3-phenylpropylamine compound can be (2R, 3R)-N-methyl-3-hydroxy-2-(2'-naphthyl)-3-phenylpropylamine, (2S, 3S)-N-methyl-3-hydroxy-2-(2'-naphthyl)-3-phenylpropylamine, (2R, 3S)-N-methyl-3-hydroxy-2-(2'-naphthyl)-3-phenylpropylamine, or (2S, 3R)-N-methyl-3-hydroxy-2-(2'-naphthyl)-3-phenylpropylamine, or any combination of (2R, 3R)-N-methyl-3-hydroxy-2-(2'-naphthyl)-3-phenylpropylamine, (2S, 3S)-N-methyl-3-hydroxy-2-(2'-naphthyl)-3-phenylpropylamine, (2R, 3s)-N-methyl-3-hydroxy-2-(2'-naphthyl)-3-phenylpropylamine, and (2S, 3R)-N-methyl-3-hydroxy-2-(2'-naphthyl)-3-phenylpropylamine.

The invention also provides methods of synthesizing amine compounds such as 3-hydroxy-pentylamine and 3-hydroxy-propylamine compounds. For example, 3-hydroxy-pentylamine and 3-hydroxy-propylamine compounds can be synthesized by a variety of organic chemistry techniques including, without limitation, carbamate reduction, N,N dimethylation, aldol reduction, and nitrile reduction. An N-methyl secondary amine compound of the invention can be synthesized by treating a primary amine with ethyl chloroformate to produce a carbamate intermediate, and then reducing the carbamate intermediate with lithium aluminum hydride. For example, the carbamate formed by treating 3-hydroxy-2-(2'-naphthyl)-3-phenylpropylamine with ethyl chloroformate can be reduced with lithium aluminum hydride to yield N-methyl-3-hydroxy-2-(2'-naphthyl)-3-phenylpropylamine. Other examples of N-methyl secondary amine compounds that can be synthesized in this manner include, without limitation, N-methyl-3-hydroxy-4,4-dimethyl-2-(2'-naphthyl)pentylamine, N-methyl-3-hydroxy-2-(2'-naphthyl)-3-phenylpropylamine, and N-methyl-3-hydroxy-4-methyl-2-(2'-naphthyl)pentylamine.

An N,N-dimethyl tertiary amine compound of the invention can be synthesized by reductive methylation of a primary amine. For example, 3-hydroxy-2-(2'-naphthyl)-3-phenylpropylamine can be treated with formalin, zinc chloride in methanol, and sodium cyanoborohydride to produce N,N-dimethyl-3-hydroxy-2-(2'-naphthyl)-3-phenylpropylamine. Another example of an N,N-dimethyl tertiary amine compound that can be synthesized in this manner is N,N-dimethyl-3-hydroxy-4-methyl-2-(2'-naphthyl)pentylamine.

A primary amine compound of the invention can be synthesized by aldol reduction. An aldehyde can be reacted with an appropriate lithiated arylacetonitrile to produce an aldol, which can then be reduced with aluminum chloride modified lithium aluminum hydride to form a primary amine. For example, 3-hydroxy-4-methyl-2-(2'-naphthyl)pentanenitrile prepared from isobutyraldehyde and 2-naphthylacetonitrile can be reduced to 3-hydroxy-4-methyl-2-(2'-naphthyl)pentylamine. Another example of a primary amine compound that can be synthesized in this manner is 3-hydroxy-2-(2'-naphthyl)-3-phenylpropylamine.

Any amine compound provided herein can be resolved to a pure enantiomer by classical resolution using enantiomerically pure acids including, without limitation, (+)- and (−)-tartaric acid, (+)- and (−)-ditoluyl-tartaric acid, and (+)- and (−)-camphorsulfonic acid. In addition, any amine compound or enantiomer thereof provided herein can be chemically converted from its free base form to a pharmaceutically acceptable salt by reacting the free base with an equivalent amount of any acid that forms a non-toxic salt. Such acids can be either inorganic or organic including, without limitation, hydrochloric acid, hydrobromic acid, fumaric acid, maleic acid, succinic acid, sulfuric acid, phosphoric acid, tartaric acid, acetic acid, citric acid, and oxalic acid. Any amine compound or pharmaceutically acceptable salt thereof can be administered to a mammal in combination with a carrier. Such carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants, chelating agents, inert gases, and the like can also be present. It will be appreciated that any amine compound provided herein that is to be administered to a mammal can contain zero, one, or more than one commonly known pharmaceutically acceptable carriers.

The invention provides methods for using amine compounds such as 3-hydroxy-pentylamine and 3-hydroxy-propylamine compounds to inhibit neurotransmitter reuptake in a mammal. The term "inhibit" as used herein with respect to neurotransmitter reuptake refers to any reduction in neurotransmitter reuptake. For example, a reduction in neurotransmitter reuptake greater than zero percent (e.g., 0.1, 0.5, 1, 2, 5, 10, 25, 50, 75, or 99 percent) is considered an inhibition of neurotransmitter reuptake. Any method can be used to assess whether or not neurotransmitter reuptake has been inhibited in a mammal. Such methods can be qualitative or quantitative. An example of a qualitative method includes assessing whether or not a mammal with depression or a related anxiety disorder experiences loss of pleasure in daily activities, significant weight loss or gain, changes in mobility (e.g., lethargy, nervousness), feelings of worthlessness, diminished ability to concentrate, or suicidal thoughts to a lesser extent following treatment with an amine compound provided herein than the extent experienced before treatment. Alternatively, such methods can be quantitative. For example, the concentration of serotonin in a platelet sample from a mammal after treatment with an amine compound can be measured and compared to the concentration of serotonin in a platelet sample from the same mammal before treatment with that amine compound. If the concentration of serotonin after treatment is reduced compared to the concentration of serotonin before treatment, then that amine compound inhibited neurotransmitter reuptake in that mammal.

To inhibit neurotransmitter reuptake, an effective amount of any amine compound provided herein can be administered to a mammal. The term "effective" as used herein refers to any amount that induces a desired level of neurotransmitter reuptake inhibition while not inducing significant toxicity in the mammal. Such an amount can be determined using the methods and materials provided herein. An effective amount of an amine compound or formulation containing an amine compound can be any amount that reduces, prevents, or eliminates an anxiety disorder upon administration to a mammal without producing significant toxicity to that mammal. Some amine compounds may have a relatively broad concentration range that is effective while others may have a relatively narrow effective concentration range. In addition, the effective amount can vary depending upon the specific mammal or anxiety disorder to be treated because certain mammals and anxiety disorders can be more or less responsive to a particular amine compound. Such effective amounts can be determined for individual amine compounds using commonly available or easily ascertainable information involving equilibrium dissociation constants, mammal toxicity concentrations, and bioavailability. For example, non-toxic amine compounds typically can be directly or indirectly administered to a mammal in any amount that reduces, prevents, or eliminates an anxiety disorder in that mammal. Using the information provided herein, such effective amounts can also be determined by routine experimentation in vitro or in vivo. For example, a patient having an anxiety disorder can receive direct administration of an amine compound in an amount close to the equilibrium dissociation constant (i.e., $K_d$) calculated from in vitro analysis sufficient to inhibit the uptake of a particular neurotransmitter. If the patient fails to respond, then the amount can be increased by, for example, two fold. After receiving this higher concentration, the patient can be monitored for both responsiveness to the treatment and toxicity symptoms, and adjustments made accordingly.

To help determine effective amounts of different amine compounds, it can be useful to refer to an effective amount equivalent based on the effective amount of a common drug used to treat anxiety disorders. For example, the direct administration of 0.30 mg/kg Prozac daily for three weeks to a mammal can be an effective amount for treating anxiety disorders. The effects produced by this effective amount can be used as a reference point to compare the effects observed for other amine compounds used at varying concentrations. Once an equivalent effect is observed, then the specific effective amount for that particular amine compound can be determined. In this case, that particular amount would be termed a Prozac effective amount equivalent.

The ability of an amine compound to inhibit neurotransmitter reuptake also can be assessed in vitro. For example, the level of serotonin reuptake can be determined by measuring the amount of radiolabeled serotonin taken up by synaptosomes purified from a tissue source abundant in serotonin transporters (e.g., rat brain cortical tissue). Rat brain cortical tissue can be isolated to produce neuronal membrane fragments such that the membrane fragments close back on themselves to form synaptosomes that retain functional serotonin transporters. The serotonin transporters concentrate serotonin by transporting it from the fluid in which the synaptosomes are suspended to the interior of the synaptosomes. If the serotonin in the suspension fluid is radiolabeled, then the level of serotonin reuptake can be measured by counting the radioactivity in the synaptosomal pellet obtained by centrifugation. The ability of an amine compound to inhibit the level of serotonin reuptake can be determined by adding different concentrations to aliquots of the same synaptosomal preparation. For example, the potency of N,N-dimethyl-3-hydroxy-4-methyl-2-(2'-naphthyl)pentylamine as an inhibitor of serotonin reuptake can be measured by (1) adding different concentrations of N,N-dimethyl-3-hydroxy-4-methyl-2-(2'-naphthyl)pentylamine to aliquots of synaptosomes purified from rat brain cortical tissue, (2) adding the same concentration of radiolabeled serotonin to each aliquot, (3) allowing the serotonin transporters to concentrate the radiolabeled serotonin in the synaptosomes, and (4) counting the radioactivity in the synaptosomal pellet of each aliquot obtained after centrifugation. Amine compounds with a higher potency will more effectively inhibit reuptake thus resulting in less detectable radioactivity in the synaptosomal pellet.

In another in vitro example, intact cultured mammalian cells expressing a particular recombinant neurotransmitter transporter can be used to assess the ability of an amine compound to inhibit neurotransmitter reuptake. For example, the potency of N-methyl-3-hydroxy-2-(2'-naphthyl)-3-phenylpropylamine as an inhibitor of norepinephrine transport can be measured using cultured mammalian cells expressing the norepinephrine transporter. In addition, the potency of a particular amine compound to inhibit multiple neurotransmitter transporters can be measured. For example, the potency of N-methyl-3-hydroxy-2-(2'-naphthyl)-3-phenylpropylamine as an inhibitor of both serotonin and norepinephrine transport can be measured using separate cultured mammalian cells expressing the serotonin transporter and cultured mammalian cells expressing the norepinephrine transporter. It is understood that measured neurotransmitter transport levels are compared to controls. Controls include, without limitation, vehicle only as well as known inhibitors such as Prozac, Paxil, Effexor, or Serzone.

In addition, the potency of an amine compound to inhibit the reuptake of different neurotransmitters can be assessed by determining the equilibrium dissociation constant (i.e., $K_d$) of that particular amine compound for a particular neurotransmitter transporter. Typically, the $K_d$ value is determined as described elsewhere (Tatsumi et al, *Eur. J. Pharmacol.*, 340:249–258 (1997)). Once determined, the $K_d$ value for a particular amine compound can be used to compare that compound's potency with the potency of other amine compounds or other known inhibitors. For example, if a particular compound has a $K_d$ of 0.3 nM for the serotonin transporter and a $K_d$ of 14.6 nM for the norepinephrine transporter, then that particular compound can be characterized as having a greater ability to inhibit serotonin reuptake compared to norepinephrine reuptake. Likewise, if a first amine compound has a $K_d$ of 0.3 nM for the serotonin transporter and a second amine compound has a $K_d$ of 6.3 nM for the serotonin transporter, then the first amine compound can be characterized as having a greater ability to inhibit serotonin reuptake compared to the second amine compound.

Various factors can influence the actual effective amount used for a particular application. For example, the frequency of administration, duration of treatment, rate of metabolism of the drug, combination of other amine compounds, and site of administration may require an increase or decrease in the actual effective amount administered.

The frequency of administration can be any frequency that reduces, prevents, or eliminates an anxiety disorder or depression in a mammal without producing significant toxicity to the mammal. For example, the frequency of administration can be from about once a day to about once a month, or more specifically, from about twice a day to about once a week. In addition, the frequency of administration can remain constant or can be variable during the duration of treatment. As with the effective amount, various factors can influence the actual frequency of administration used for a particular application. For example, the effective amount, duration of treatment, rate of metabolism of the drug, combination of other amine compounds, and site of administration may require an increase or decrease in administration frequency.

An effective duration for amine compound administration can be any duration that reduces, prevents, or eliminates an anxiety disorder in a mammal without producing significant toxicity to the mammal. Thus, the effective duration can vary from several days to several weeks, months, or years. In general, the effective duration for the treatment of an anxiety disorder can range in duration from several days to several years. Once the amine compound administrations are stopped, however, the treated anxiety disorder may return. Thus, the effective duration for the prevention of an anxiety disorder can last in some cases for as long as the individual is alive.

Multiple factors can influence the actual effective duration used for a particular treatment or prevention regimen. For example, an effective duration can vary with the frequency of amine compound administration, effective amine compound amount, combination of multiple amine compounds, and site of administration. It is noted that diagnostic algorithm methods can be devised to determine or reflect appropriate effective doses, durations, and frequencies.

The level of toxicity, if any, can be determined by assessing a mammal's clinical signs and symptoms before and after administering a known amount of a particular composition. It is noted that the effective amount of a particular composition administered to a mammal can be adjusted according to a desired outcome as well as the mammal's response and level of toxicity. Significant toxicity can vary for each particular mammal and each particular composition.

Any combination of amine compounds can be administered to a mammal. For example, two amine compounds can be administered together to a mammal to inhibit norepinephrine reuptake in that mammal. In another example, one or more compounds that can inhibit serotonin reuptake and one or more compounds that can inhibit dopamine reuptake can be administered together to a mammal to inhibit both serotonin and dopamine reuptake in that mammal. The efficacy of such combinations can be assessed using the methods and materials provided herein.

An amine compound or combination of amine compounds can be administered to any part of a mammal's body. For example, an amine compound can be delivered to, without limitation, spinal fluid, blood, lungs, intestines, muscle tissues, skin, joints, peritoneal cavity, or brain of a mammal. In addition, an amine compound or combination of amine compounds can be administered intravenously, intraperitoneally, intramuscularly, subcutaneously, intrathecally, intracerebroventricularly, or intradermally, orally, by inhalation, or by gradual perfusion over time. The duration of treatment can be any length of time from as short as one day to as long as the life span of the mammal (e.g., many years). For example, an amine compound can be administered daily for three months or ten years. It is also noted that the frequency of treatment can be variable. For example, an amine compound can be administered once (or twice, three times, etc.) daily, weekly, monthly, or yearly.

The invention will be further described in the following examples, which do not limit the scope of the invention described in the claims.

EXAMPLES

Example 1

Human Transporter Binding Studies

Human embryonic kidney (HEK-293) cells stably transfected and constitutively expressing the human norepinephrine transporter (hNET; Pacholczyk et al., *Nature*, 350: 350–354 (1991)), the human dopamine transporter (hDAT; Pristupa et al., *Mol. Pharmacol.*, 45:125–135 (1994)), or the human serotonin transporter (hSERT; Ramamoorthy et al., *Proc. Natl. Acad. Sci. U.S.A.* 90:2542–2546 (1993)) were grown and passaged in 150-mm petri dishes with 17.5 ml of Dulbecco's modified Eagle's medium (MEM; Mediatech Inc., Herndon, Va.) containing 0.1 mM non-essential amino acid solution for MEM (Mediatech Inc.), 5% (v/v) fetal clone bovine serum product (Hyclone Laboratories, Logan, Utah), and 1 U/μL penicillin/streptomycin solution (Mediatech Inc.). The cells were incubated in 10% $CO_2$, 90% air at 37° C. and 100% humidity. The hNET cell cultures contained 250 μg/mL geneticin sulfate. The cells were grown to 70–80% confluency prior to harvesting.

Cell membranes containing hSERT, hNET, or hDAT were prepared from the cell lines to assay ligand binding for each of the transporters. Briefly, the cell medium was removed by aspiration, and the cells were washed with 4 mL modified Puck's D1 solution (solution 1; Richelson et al. in "Methods in Neurotransmitter Receptor Analysis" Yamamura, H. I.; Enna, S. J.; Kuhar, M. J. Eds.; New York, Raven Press, 1990, pp 147–175). The washed cells were incubated for 5 minutes at 38° C. in 10 mL solution 1 containing 100 mM ethylene glycol-bis N,N,N',N'-tetraacetic acid (EGTA). The cells were then scraped from the flask surface with a rubber spatula, placed into a centrifuge tube, and collected by centrifugation at 1000×g for 5 minutes at 4° C. The resulting supernatant was discarded, and the cell pellet was resuspended in 0.5 to 1.0 mL of the appropriate binding buffer (described below). The resuspended cell pellet was homogenized using a Polytron for 10 seconds at setting 6. The resulting homogenate was centrifuged at about 36,000×g for 10 minutes at 4° C. The supernatant was discarded, and the pellet was resuspended in the same volume of the appropriate binding buffer and centrifuged again. The supernatant was discarded, and the final pellet containing cell membranes was resuspended in the appropriate binding buffer and stored at −80° C. until use. The final protein concentration was determined by the Lowry assay using bovine serum albumin as a standard (Lowry et al., *J. Biol. Chem.* 193:265–275 (1951)).

Radioligand binding assays for the indicated transporters were performed as follows. To assess binding to the cloned hSERT, cells expressing hSERT were homogenized in 50 mM Tris-HCl with 120 mM NaCl and 5 mM KCl (pH 7.4). The binding reaction consisted of 30 μg cell membrane protein, 1.0 nM [$^3$H]imipramine (imipramine hydrochloride, benzene ring-$^3$H, specific activity 46.5 Ci/mmol; Dupont New England Nuclear, Boston, Mass.), and varying concentrations of either unlabeled imipramine or the test amine compound. A reaction to determine non-specific binding consisted of 15 μg cell membrane protein, 1.0 nM [$^3$H] imipramine, and 1 μM final concentration of unlabeled imipramine. The reactions were incubated at 22° C. for 60 minutes. Following incubation, the reactions were terminated by rapid filtration through separate GF/B filter strips pretreated with 0.2% polyethylenimine in a 48-well Brandel cell harvester. The cell membrane-containing filter strips were then rinsed five times with ice-cold 0.9% NaCl. After rinsing, individual filters were cut from the strip and placed in a scintillation vial containing 6.5 mL of Redi-Safe (Beckman Instruments, Fullerton, Calif.). Radioactivity was measured with a Beckman liquid scintillation counter (LS 5000TD).

To assess binding to the cloned hNET, cells expressing hNET were homogenized in 50 mM Tris-HCl with 300 mM NaCl and 5 mM KCl (pH 7.4). The binding reaction consisted of 25 μg cell membrane protein, 0.5 nM [$^3$H]nisoxetine (nisoxetine HCl, [N-methyl-$^3$H], specific activity 85.0 Ci/mmol; Amersham, Arlington Hts., Ill.), and varying concentrations of either unlabeled nisoxetine or the test amine compound. A reaction to determine non-specific binding consisted of 25 μg cell membrane protein, 0.5 nM [$^3$H] nisoxetine, and 1 μM final concentration of unlabeled nisoxetine. The reactions were incubated at 22° C. for 60 minutes. Following incubation, the reactions were terminated by rapid filtration through separate GF/B filter strips pretreated with 0.2% polyethylenimine in a 48-well Brandel cell harvester. The cell membrane-containing filter strips were then rinsed five times with ice-cold 0.9% NaCl. After rinsing, individual filters were cut from the strip and placed in a scintillation vial containing 6.5 mL of Redi-Safe (Beckman Instruments, Fullerton, Calif.). Radioactivity was measured with a Beckman liquid scintillation counter (LS 5000TD).

To assess binding to the cloned hDAT, cells expressing hDAT were homogenized in 50 mM Tris-HCl with 120 mM NaCl (pH 7.4). The binding reaction contained 30 μg cell membrane protein, 1 nM [$^3$H]WIN35428 (WIN35428, [N-methyl-$^3$H], specific activity 83.5 Ci/mmol; Dupont New England Nuclear, Boston, Mass.), and varying concentrations of either unlabeled WIN35428 or the test amine compound. A reaction to determine non-specific binding contained 30 μg cell membrane protein, 1 nM [$^3$H] WIN35428, and 10 μM final concentration of unlabeled WIN35428. The reactions were incubated at 22° C. for 1 hour. Following incubation, the reactions were terminated by rapid filtration through separate GF/B filter strips pretreated with 0.2% polyethylenimine in a 48-well Brandel cell harvester. The cell membrane-containing filter strips were then rinsed five times with ice-cold 0.9% NaCl. After rinsing, individual filters were cut from the strip and placed in a scintillation vial containing 6.5 mL of Redi-Safe (Beckman Instruments, Fullerton, Calif.). Radioactivity was measured with a Beckman liquid scintillation counter (LS 5000TD).

Following the radioligand binding assays, the data were analyzed using the LIGAND program (Munson and Rodbard, *Analyt. Biochem.*, 107:220–239 (1980)) to provide values for the equilibrium dissociation constants ($K_d$). The program was modified to calculate the Hill coefficient (nH). Data are presented as geometric mean ±S.E.M. of at least three independent experiments. One-component models and two-component models were compared using the root mean square error of each fit and the F test. A low $K_d$ for a compound indicates strong binding to the transporter (i.e., reuptake inhibition).

The compounds exhibited $K_d$ values ranging from strong to weak transporter binding. Compound A exhibited the strongest binding to hNET of all the compounds tested. In addition, compound A exhibited greater specificity for hNET than for hSERT or hDAT. Compound B showed greater specificity for hDAT than the parent analogue venlfaxine. Compound C was a more potent inhibitor of hSERT than of hNET or hDAT. Compound C also exhibited greater specificity for all three transporters compared to venlafaxine, indicating that it is a more potent transporter inhibitor. In addition, compounds C1 and C2 showed greater specificity for hSERT than for hNET of hDAT, and greater specificity for all three transporters compared to venlafaxine. Compound D exhibited stronger binding to hSERT than to hNET or hDAT, and was a more potent inhibitor of all three transporters compared to vanlafaxine. Compound D1 showed similar specificities for hNET and hSERT, which were greater than that for hDAT, indicating that it was a more potent inhibitor of hNET and hSERT compared to hDAT. Compound D2 exhibited greater specificity for hSERT than for hNET or hDAT. Both compounds D1 and D2 showed greater specificity for all three transporters compared to venlafaxine. Compounds E and F exhibited greater specificity for hDAT compared to vanlafaxine. These data demonstrated that in vitro human transporter binding studies can be used to determine the ability of an amine compound to inhibit neurotransmitter transport. These data also demonstrated that amine compounds inhibit neurotransmitter transport in varying degrees at different transporters.

TABLE 1

Human transporter binding data

| Compound | hNET $K_d$ (nM) | SEM | hSERT $K_d$ (nM) | SEM | hDAT $K_d$ (nM) | SEM |
|---|---|---|---|---|---|---|
| Nisoxetine | 2.4 | 0.1 | | | | |
| Imipramine | | | 1.7 | 0.1 | | |
| WIN35428 | | | | | 29 | 1 |
| Desipramine | 0.83 | 0.05 | 17.6 | 0.7 | 3190 | 40 |
| Paroxetine | 40 | 2 | 0.13 | 0.01 | 490 | 20 |
| Sertraline | 420 | 20 | 0.29 | 0.01 | 25 | 2 |
| Venlafaxine | 1060 | 40 | 8.9 | 0.3 | 9300 | 50 |
| A | 0.25 | 0.03 | 6.3 | 0.3 | 130 | 10 |
| B | | | | | 390 | 10 |
| C | 329 | 2 | 5.7 | 0.5 | 880 | 80 |
| C1 | 150 | 20 | 7 | 1 | 1280 | 50 |
| C2 | 140 | 10 | 15.1 | 0.9 | 1600 | 200 |
| D | 14.6 | 0.7 | 0.30 | 0.04 | 180 | 20 |
| D1 | 7.4 | 0.4 | 4.2 | 0.3 | 150 | 10 |
| D2 | 60 | 6 | 2.6 | 0.4 | 800 | 150 |
| E | | | | | 420 | 10 |

A: racemic mixture of (2R, 3R)- and (2S, 3S)-N-methyl-3-hydroxy-2-(2'-naphthyl)-3-phenylpropylamine.
B: racemic mixture of (2S, 3R)- and (2R, 3S)-N-methyl-3-hydroxy-2-(2'-naphthyl)-3-phenylpropylamine.
C: racemic mixture of (2R, 3S)- and (2S, 3R)-3-hydroxy-4-methyl-2-(2'-naphthyl)pentylamine.
C1: (2R, 3S)-3-hydroxy-4-methyl-2-(2'-naphthyl)pentylamine.
C2: (2S, 3R)-3-hydroxy-4-methyl-2-(2'-naphthyl)pentylamine.
D: racemic mixture of (2R, 3S)- and (2S, 3R)-N,N-dimethyl-3-hydroxy-4-methyl-2-(2'naphthyl)pentylamine.
D1: (2R, 3S)-N,N-dimethyl-3-hydroxy-4-methyl-2-(2'-naphthyl)pentylamine.
D2: (2S, 3R)-N,N-dimethyl-3-hydroxy-4-methyl-2-(2'-naphthyl)pentylamine.
E: racemic mixture of (2S, 3R)- and (2R, 3S)-3-hydroxy-2-(2'naphthyl)-3-phenylpropylamine.
F: racemic mixture of (2S, 3R)- and (2R, 3S)-N,N-dimethyl-3-hydroxy-2-(2'-naphthyl)-3-phenylpropylamine.

Example 2

Neurotransmitter Reuptake in Rat Brain Synaptosomes

Cortical, striatal, and hippocampal tissues are dissected from freshly decapitated male Sprague-Dawley rats (125–250 g; Harlan Sprague-Dawley, Indianapolis, Ind., USA). The dissected tissues are separately homogenized in 20 volumes of ice-cold 0.32 M sucrose containing 11 mM glucose (pH 7.4) in a glass Potter-Elvehjem homogenizer with Teflon® pestle (8 strokes, 900 rpm). The homogenates are centrifuged at 1,000×g for 10 minutes. The resulting supernatant is decanted and further centrifuged at 20,000×g for 20 minutes. The supernatant is discarded, and the synaptosomes contained in the pellet are gently resuspended in oxygenated incubation buffer containing 10 mM glucose, 20 mM HEPES, 145 mM NaCl, 4.5 mM KCl, 1.2 mM $MgCl_2$, and 1.5 mM $CaCl_2$ (pH 7.4). The synaptosomal protein concentration is determined by the Lowry method using bovine serum albumin as a standard (Lowry et al., *J. Biol. Chem.* 193:265–275 (1951)).

Synaptosomal protein (1.0–2.5 mg) is suspended 1 mL oxygenated incubation buffer containing 10 μM pargyline to inhibit monoamine oxidase activity and 0.2 mg/mL sodium ascorbate. Separate reaction tubes containing 8 nM levo-[ring-2,5,6-$^3$H]norepinephrine ([$^3$H]NE; 43.7 Ci/mmol; New England Nuclear, Boston, Mass.), 4 nM 5-[1,2-$^3$H (N)]hydroxytryptamine binoxalate ([$^3$H]5-HT; 23.4 Ci/mmol; New England Nuclear), or 2 nM [7,8-$^3$H]dopamine (DA) ([$^3$H]DA; 47 Ci/mmol; Amersham, Arlington Heights, Ill.) are preincubated for 5 minutes at 37° C. in a shaking water bath (80 oscillations/minute) in the presence of the test amine compound. After preincubation, the neurotransmitter reuptake reaction is initiated by the addition of synaptosomal protein. The reaction is stopped after 5 minutes by adding 4 mL ice-cold 0.9% (w/v) sodium chloride. The stopped reactions are rapidly filtered through a Whatman GF/B glass fiber filter in a 48-place Brandel cell harvester. The filters containing deposited synaptosomes are then washed with an additional 8 mL of wash buffer. The washed filters are placed in a scintillation vial containing 5 mL of Redi-Safe (Beckman Instruments, Fullerton, Calif.) and counted. Specific reuptake is calculated as the difference between the total reuptake (zero unlabelled ligand) and nonspecific reuptake (excess unlabelled ligand).

Example 3

Testing Amine Compounds in Animals and Humans

Test amine compounds are prepared by formulating the amine compounds with a pharmaceutically acceptable carrier such as saline. To determine the toxic levels of each amine compound, non-human mammals (e.g., mice, rats, or lower primates) are used. Briefly, 100 rats are randomly separated into five groups of 20. One group, group A, receives a placebo, while the other groups receive a particular dose of a compound, e.g., group B receives the compound at 1 μg/kg, group C receives the compound at 100 μg/kg, group D receives the compound at 10 mg/kg, and group E receives the compound at 100 mg/kg. The rats in each group are dosed according to a prescribed plan for a predetermined period of time, and toxic levels of the administered compound are determined by measuring survival or other clinical signs such as aggressiveness, irregular bleeding, and appetite. After determining the toxic level of an amine compound, tolerability and pharmacokinetic studies are performed in normal humans.

Once the toxicity, tolerability, and pharmacokinetic studies have been performed for an amine compound, 100 human subjects having an anxiety disorder are selected for clinical trials. The subjects are separated into two groups of 50. One group, group A, receives a placebo, while the other group, group B, receives the highest possible dose of a compound that has been determined not to be toxic to a mammal. The subjects in each group are dosed according to a prescribed plan for a predetermined period of time, and the ability of the administered amine compound to alleviate anxiety disorder symptoms are determined using standard clinical methods that are used to assess anxiety disorders.

Example 4

Synthesis of N-methyl-3-hydroxy-2-(2'-naphthyl)-3-phenylpropylamine, HCl Salt

Synthesis of carbamate A 3-hydroxy-2-(2'-naphthyl)-3-phenylpropylamine (1.32 g, 4.76 mmol) was dissolved in $CH_2Cl_2$ (20 ml), and ethyl chloroformate (550 μL, 5.75 mmol) was added. The resulting milky suspension was stirred for 4 hours at room temperature. After stirring, water (130 mL) was added to aid in the separation of the aqueous and organic phases. The aqueous phase was extracted 4 times with 100 mL ethyl acetate, and the organic phases were combined, dried over $K_2CO_3$, filtered, and concentrated in vacuo to yield carbamate A (1.65 g, 99%). $^1$H NMR ($CDCl_3$) analysis: δ 1.20(t, J=7.1 Hz, 3H), 3.12(s, 1H), 3.30–3.32(m, 1H), 3.71–3.74(m, 1H), 3.86–3.88(m, 1H) 4.08–14.11(q,J=14.2 Hz,2H),4.87(s, br, 1H), 5.03(d,J=8 Hz), 7.15–7.2(m, 6H),7.4–7.48(m, 2H), 7.52(s, 1H), 7.1–7.8(m,3H). $^{13}$C NMR ($CDCl_3$) analysis: δ 14.48, 42.88, 53.56, 60.92, ~76.4, 125.58, 125.94, 126.41, 126.61, 127.29, 127.40, 127.46, 127.58, 128.05, 132.34, 133.23, 137.22, 142.21, 157.15.

Reduction of carbamate A to N-methyl-3-hydroxy-2-(2′-naphthyl)-3-phenylpropylamine A round bottom flask equipped with a stir bar and water condenser was charged with carbamate A (1.47 g, 4.21 mmol), lithium aluminum hydride ($LiAlH_4$; 0.39 g, 10.3 mmol), and dry tetrahydrofuran (THF; 150 mL). The mixture was refluxed under $N_2$ for 10–12 hours, yielding a blue-gray suspension. The reaction was quenched by adding 1 mL water. After quenching the reaction, 10% aqueous NaOH was added with stirring to yield a white solid and a clear organic layer. The organic layer was decanted, and 10 mL water was added to the solid. After mixing for 15 minutes, the white solid was extracted four times with 20 mL diethyl ether, and the ether extracts were pooled. The pooled extracts were dried over $K_2CO_3$, filtered, and concentrated in vacuo to yield N-methyl-3-hydroxy-2-(2′-naphthyl)-3-phenylpropylamine free base (1.14 g, 3.91 mmol, 92.9%). This free base was converted to the HCl salt by treatment with concentrated HCl in methanol, followed by concentration in vacuo. $^1$H NMR ($CDCl_3$) analysis: δ 2.72(s, 3H), 3.24(s, br, 1H), 3.21(d, J=10.10 Hz, 1H), 5.17(d, J=9.15 Hz, 1H), 5.45(s, br, 1 H), 7.04–7.14(m, 4H), 7.21–7.22(2H), 7.40–7.46(m, 3H), 7.61–7.71(m, 3H). $^{13}$C NMR ($CDCl_3$) analysis: δ 34.13, 49.10, 54.87, 79.23, 125.89, 126.01, 126.22, 127.00, 127.54, 127.70, 127.86, 128.28, 128.40, 128.47, 132.49, 133.21, 135.22, 141.67.

Example 5

Synthesis of N-methyl-3-hydroxy-4,4-dimethyl-2-(2′-naphthyl)pentylamine, HCl salt Synthesis of carbamate B 3-hydroxy-4,4-dimethyl-2-(2′-naphthyl)pentylamine (207 mg, 0.706 mmol) was treated with ethyl chloroformate (81 μL, 0.85 mmol) and triethylamine (0.9 mL, 6.46 mmol) as described in Example 3 to yield carbamate B (130.5 mg, 56%).

Synthesis of N-methyl-3-hydroxy-4,4-dimethyl-2-(2′-naphthyl)pentylamine from carbamate B A three-necked round bottom flask equipped with a stir bar and water condenser was charged with carbamate B (122.3 mg, 0.37 mmol), $LiAlH_4$ (31 mg, 0.82 mmol) and dry THF (10 mL). The mixture was refluxed under $N_2$ for 4 hours. After refluxing, the reaction was quenched by stirring for 1 hour in the presence of 20 mL ether and 10 mL 10% $H_2SO_4$. The acid layer was separated and washed two times with 5 mL ether. The ether washed acid layer was then cooled to 0° C. in an ice bath and adjusted to pH 11 with 2N NaOH. The aqueous layer was then extracted four times with 10 mL ether, and the extracts pooled. The pooled extracts were washed with 25 mL brine and dried over $K_2CO_3$ overnight. After drying, the pooled extracts were filtered and concentrated in vacuo to yield N-methyl-3-hydroxy-4,4-dimethyl-2-(2′-naphthyl)pentylamine free base (45 mg, 45%). This free base was converted to the HCl salt as described in Example 3. $^1$NMR ($CD_3OD$) analysis: δ 0.92 (s, 9H), 2.65 (s, 3H), 3.15–3.19 (dd, 1H), 3.38–3.44 (dd, 1H), 3.54–3.60 (dd, 1H), 3.87–3.88 (d, 1H), 7.42–7.48 (m, 3H), 7.83–7.88 (m, 4H). $^{13}$C NMR ($CD_3OD$) analysis: δ27.54, 35.10, 38.35, 46.82, 56.27, 83.89, 127.74, 127.98, 128.33, 129.04, 129.50, 129.55, 131.0, 135.10, 135.92, 140.87.

Example 6

Synthesis of 3-hydroxy-2-(2′-naphthyl)-3-phenylpropylamine, HCl Salt 3-hydroxy-2-(2′-naphthyl)-3-phenylpropionitrile (0.77 g, 2.8 mmol) was reduced according to the procedure of Carlier et al. (Carlier et al., *Org. Lett.*, 2: 2443–2445 (2000)) to yield 3-hydroxy-2-(2′-naphthyl)-3-phenylpropylamine free base (0.76 g, 98%). This free base was converted to the HCl salt as described in Example 3. $^1$H NMR ($CD_3OD$) analysis: δ 3.3–3.33(1H), 3.40–3.48(m, 2H), 5.08(d, J=5.30 Hz, 1H), 7.16–7.83(m, 12H). $^{13}$C NMR ($CD_3OD$) analysis: δ42.56, 52.66, 76.83, 127.09, 127.23, 127.70, 127.92, 128.63, 128.75, 128.83, 129.12, 129.27, 129.71, 134.47, 134.81, 135.37, 143.25.

Example 7

Synthesis of N-methyl-3-hydroxy-2-(2′-naphthyl)-3-phenylpropylamine, HCl salt

Synthesis of carbamate D 3-hydroxy-2-(2′-naphthyl)-3-phenylpropylamine (0.26 g, 0.95 mmol) was treated with ethyl chloroformate as described in Example 3 yielding carbamate D (0.22 g, 67%). $^1$H NMR ($CDCl_3$) analysis: δ 1.15(t, J=7.10 Hz, 3H), 2.63(s, 1H), 3.24–3.42(m, 2H), 3.67–3.73(dt, J=7.1, 13.5 Hz, 1H), 4.01–4.06(dd, 7.10, 14.2 Hz), 4.60(br, s, 1H), 5.0(d, 5.5 Hz), 7.22–7.82(m, 12H). $^{13}$C NMR ($CDCl_3$) analysis: δ14.62, 42.98, 53.99, 61.06, 75.5, 125.89, 126.18, 126.50, 126.88, 127.69, 127.77, 127.86, 128.37, 132.79, 133.40, 135.96, 141.86.

Reduction of Carbamate D to N-methyl-3-hydroxy-2-(2′naphthyl)-3-phenylpropylamine Carbamate D (190 mg, 0.63 mmol) was reduced with $LiAlH_4$ as described in Example 3 yielding N-methyl-3-hydroxy-2-(2′-naphthyl)-3-phenylpropylamine free base (45.9 mg, 25%). This free base was converted to the HCl salt as described in Example 3. $^1$NMR ($CD_3OD$) analysis: δ 2.64(s, 3H), 3.39–3.42(dd, J=4.55, 11.90 Hz, 1H), 3.52–3.62 (m, 2H), 5.09(d, J=5.30 Hz, 1H), 7.11–7.83(m, 12H). $^{13}$C NMR ($CD_3OD$) analysis: δ 34.41, 51.65, 52.40, 76.83, 127.16, 127.26, 127.70, 127.96, 128.62, 128.72, 128.84, 129.07, 129.28, 129.70, 134.48, 134.79, 135.09, 143.0.

Example 8

Synthesis of N,N-dimethyl-3-hydroxy-2-(2'-naphthyl)-3-phenylpropylamine, HCl salt 3-hydroxy-2-(2'-naphthyl)-3-phenylpropylamine (0.20 g, 0.73 mmol) was treated with formalin, $ZnCl_2$ (253 mg, 1.86 mmol), and $NaBH_3CN$ (140 mg, 2.23 mmol) according to the procedure of Carlier et al. (Carlier et al., *Bioorg. Med. Chem. Lett.*, 8:487–492 (1998)) to yield N,N-dimethyl-3-hydroxy-2-(2'-naphthyl)-3-phenylpropylamine free base (0.179 g, 80%). This free base was converted to the HCl salt as described in Example 3. $^1$H NMR ($CD_3OD$) analysis: δ 2.84(s, 3H), 2.87(s, 3H), 3.55–3.59(dd, J=5.0, 13.0 Hz, 1H), 3.67–3.72(dt, J=5.0, 10.1 Hz, 1H), 3.84–3.88(dd, J =10.0, 13.0 Hz, 1H), 5.08(d, J=5.0 Hz, 1H), 7.07–7.87(m, 12H). $^{13}$C NMR ($CD_3OD$) analysis: δ 43.57, 45.18, 49.84, 60.87, 76.99, 127.25, 127.32, 127.70, 128.04, 128.64, 128.73, 128.89, 129.04, 129.36, 129.76, 134.50, 134.66, 134.80, 142.77.

Example 9

Synthesis of 3-hydroxy-4-methyl-2-(2'-naphthyl)pentylamine, HCl salt

Synthesis of Aldol E 3-hydroxy-4-methyl-2-(2'-naphthyl)pentanenitrile was prepared from 2-naphthylacetonitrile and isobutyraldehyde according to the procedure of Carlier et al., (Carlier et al., *J. Org. Chem.*, 60:7511–7517 (1995)) producing aldol E in 58% yield.

Reduction of aldol E to 3-hydroxy-4-methyl-2-(2'-naphthyl)pentylamine

Aldol E (1.16 g, 4.9 mmol) was reduced to 3-hydroxy-4-methyl-2-(2'-naphthyl)pentylamine free base (0.80 g, 59%) according to the procedure of Carlier et al., (Carlier et al., *J. Org. Chem.*, 60:7511–7517 (1995)). This free base was converted to the HCl salt as described in Example 3. $^1$H-NMR ($CD_3OD$) analysis: δ 0.866–0.960 (m, 6H), 1.281–1.443 (m, 1H), 3.171–3.319 (m, 2H), 3.620–3.701 (m, 1H), 3.913 (d, J=7.1 Hz, 1H), 7.412–7.511 (m, 3H), 7.803–7.923 (m, 4H). $^{13}$C-NMR ($d_4$-DMSO) analysis: δ 14.45, 20.31, 29.59, 42.57, 47.38, 76.67, 125.77, 126.12, 126.19, 127.33 127.50, 127.62, 128.41, 132.31, 133.14, 137.12 (Expected: 16C, Found: 16C). MS ($CI^+$): Calcd for $C_{16}H_{22}NOCl$: 279.14, Found: 244.2 (M−Cl).

Example 10

Resolution of 3-hydroxy-4-methyl-2-(2'-naphthyl)pentylamine into the (+)-isomer

A 100 mL round bottom flask equipped with a stir bar was charged with 1.52 g 3-hydroxy-4-methyl-2-(2'-naphthyl)pentylamine (6.2 mmol), 0.979 g (S)-(+)-mandelic acid (6.4 mmol), and 30 mL ethanol. After stirring at 60° C. for 1 hour, the homogenous mixture was allowed to cool to room temperature yielding a solid. The solid was collected by filtration and then recrystallized twice from hot ethanol to yield the diastereomerically pure mandelate salt. The mandelate salt was treated with 2N NaOH to generate the free base, which was extracted three times with 50 mL diethyl ether. The extracts were pooled and treated with HCl gas to yield the (+) isomer of 3-hydroxy-4-methyl-2-(2'-naphthyl)pentylamine HCl salt (0.504 g, 28.9 %). NMR and Mass spectral data were identical to that of 3-hydroxy-4-methyl-2-(2'-naphthyl)pentylamine. [α]=+30.3° (c 0.132, MeOH).

Example 11

Resolution of 3-hydroxy-4-methyl-2-(2'-naphthyl)pentylamine into the (−)-isomer

A 100 mL round bottom flask equipped with a stir bar was charged with 1.52 g 3-hydroxy-4-methyl-2-(2'-naphthyl)pentylamine (6.2 mmol), 0.975 g (R)-(−)-mandelic acid (6.4 mmol), and 30 mL ethanol were combined as described in Example 9 to yield the (−) isomer of 3-hydroxy-4-methyl-2-(2'-naphthyl)pentylamine (0.493 g, 28.3%). NMR and Mass spectral data were identical to that of 3-hydroxy-4-methyl-2-(2'-naphthyl)pentylamine. [α]=−29.8° (c 0.134, MeOH).

Example 12

Synthesis of N,N-dimethyl-3-hydroxy-4-methyl-2-(2'-naphthyl)pentylamine, HCl salt 3-hydroxy-4-methyl-2-(2'-naphthyl)pentylamine (201 mg, 0.7 mmol) was converted to N,N-dimethyl-3-hydroxy-4-methyl-2-(2'-naphthyl)pentylamine HCl salt (216 mg, 98% yield) using the N,N-dimethylation procedure of Carlier et al. (Carlier et al., *Bioorg. Med. Chem. Lett.*, 8:487–492 (1998)) followed by treatment with methanolic HCl. $^1$H-NMR ($CD_3OD$) analysis: δ 1.064–1.098 (m, 6H), 1.511–1.586 (m, 1H), 3.113 (s, 6H), 3.538–3.683 (m, 2H), 4.062 (dd, J=7.2 Hz, 12.4 Hz, 1H), 4.130 (dd, J=1.9 Hz, 9.3 Hz, 1H), 7.635–7.726 (m, 3H), 8.038–8.119 (m, 4H). $^{13}$C-NMR ($CD_3OD$) analysis: δ 14.80, 20.76, 31.46, 44.29, 44.85, 46.18, 62.28, 80.70, 126.86, 127.65, 127.90, 128.93, 129.01, 129.08, 130.58, 134.72, 135.43, 137.10 (Expected: 18C, Found: 18C). MS ($CI^+$): Calcd for $C_{18}H_{26}NOCl$: 307.17, Found: 272.2 (M−Cl).

Example 13

Resolution of N,N-dimethyl-3-hydroxy-4-methyl-2-(2'-naphthyl)pentylamine into the (+)-isomer The (+) isomer of 3-hydroxy-4-methyl-2-(2'-naphthyl)pentylamine (103 mg, 0.37 mmol) was converted to the (+) isomer of N,N-dimethyl-3-hydroxy-4-methyl-2-(2'-naphthyl)pentylamine HCl salt (114 mg, 100%) using the N,N-dimethylation procedure of Carlier et al. (Carlier et al., *Bioorg. Med. Chem. Lett.*, 8:487–492 (1998)) followed by treatment with methanolic HCl. NMR and Mass spectral data were identical to that of N,N-dimethyl-3-hydroxy-4-methyl-2-(2'-naphthyl)pentylamine. [α]=+4.2° (c 0.190, MeOH).

Example 14

Resolution of N,N-dimethyl-3-hydroxy-4-methyl-2-(2'-naphthyl)pentylamine into the (−)-isomer The (−) isomer of 3-hydroxy-4-methyl-2-(2'-naphthyl)pentylamine (104 mg, 0.37 mmol) was converted to the (−) isomer of N-dimethyl-3-hydroxy-4-methyl-2-(2'-naphthyl)pentylamine HCl salt (114 mg, 100%) using the N,N-dimethylation procedure of Carlier et al. (Carlier et al.,

*Bioorg. Med. Chem. Lett.*, 8:487–492 (1998)) followed by treatment with methanolic HCl. NMR and Mass spectral data were identical to that of N,N-dimethyl-3-hydroxy-4-methyl-2-(2'-naphthyl)pentylamine. [α]=−3.8° (c 0.260, MeOH).

Example 15

Synthesis of N-methyl-3-hydroxy-4-methyl-2-(2'-naphthyl)pentylamine, HCl salt

Synthesis of carbamate C

A weighed amount of 3-hydroxy-4-methyl-2-(2'-naphthyl)pentylamine is treated with ethyl chloroformate as described in Example 3 to yield carbamate C.

Reduction of Carbamate C to N-methyl-3-hydroxy-4-methyl-2-(2'-naphthyl)pentylamine A round bottom flask equipped with a stir bar and water condenser is charged with a weighed amount of carbamate C, a weighed amount of LiAlH$_4$, and a measured volume of dry THF. The mixture is refluxed under N$_2$ for several hours, and the reaction is quenched by adding water. After quenching the reaction, aqueous NaOH is added with stirring to yield a white solid and a clear organic layer. The organic layer is decanted, and water is added to the solid. After mixing for 15 minutes, the white solid is extracted four times with diethyl ether, and the ether extracts are pooled. The pooled extracts are dried over K$_2$CO$_3$, filtered, and concentrated in vacuo to yield N-methyl-3-hydroxy-4-methyl-2-(2'-naphthyl)pentylamine free base. This free base is converted to the HCl salt by treatment with concentrated HCl in methanol, followed by concentration in vacuo.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising N-methyl-3-hydroxy-4,4-dimethyl-2-(2'naphthyl)pentylamine.

2. The composition of claim 1, wherein said N-methyl-3-hydroxy-4,4-dimethyl-2-(2'naphthyl) pentylamine comprises (2R, 3R)-N-methyl-3-hydroxy-4,4-dimethyl-2-(2'naphthyl) pentylamine or (2S, 3S)-N-methyl-3-hydroxy-4,4-dimethyl-2-(2'-naphthyl)pentylamine.

3. The composition of claim 1, wherein said N-methyl-3-hydroxy-4,4-dimethyl-2-(2'naphthyl) pentylamine comprises (2R, 3S)-N-methyl-3-hydroxy-4,4-dimethyl-2-(2'naphthyl) pentylamine or (2S, 3R)-N-methyl-3-hydroxy-4,4-dimethyl-2-(2'-naphthyl)pentylamine.

4. The composition of claim 1, wherein said N-methyl-3-hydroxy-4,4-dimethyl-2-(2'-naphthyl) pentylamine comprises:

a) two of the compounds selected from the group consisting of(2R, 3R)-N-methyl-3-hydroxy-4,4-dimethyl-2-(2'-naphthyl)pentylamine,(2S, 3S)-N-methyl-3-hydroxy-4,4-dimethyl-2-(2'-naphthyl)pentylamine, (2R, 3S)-N-methyl-3-hydroxy-4,4-dimethyl-2-(2'-naphthyl) pentylamime, and (2S, 3R)-N-methyl-3-hydroxy-4,4-dimethyl-2-(2'naphthyl)pentylamine; or b) three of the compounds selected from the group consisting of (2R, 3R)-N-methyl-3hydroxy-4,4-dimethyl-2-(2'-naphthyl)pentylamine, (2S, 3 S)-N-methyl-3-hydroxy-4,4-dimethyl-2-(2'-naphthyl)pentylamine, (2R, 3S)-N-methyl-3-hydroxy-4,4-dimethyl-2-(2'naphthyl)pentylamine, and (2S, 3R)-N-methyl-3-hydroxy-4,4-dimethyl-2-(2'naphthyl)pentylamine; or c) (2R, 3R)-N-methyl-3 -hydroxy-4,4-dimethyl-2-(2'-naphthyl)pentylamine, (2S, 3S)-N-methyl-3 -hydroxy-4,4-dimethyl-2-(2'-naphthyl)pentylamine, (2R, 3 S)-N-methyl-3-hydroxy-4,4-dimethyl-2-(2'-naphthyl) pentylamine, and (2S, 3R)-N-methyl-3-hydroxy-4,4-dimethyl-2-(2'-naphthyl)pentylamine.

5. The composition of claim 1, wherein said composition comprises a pharmaceutically acceptable carrier.

* * * * *

UNITED STATES PATENT AND TRADEMARK OFFICE
CERTIFICATE OF CORRECTION

PATENT NO. : 7,214,826 B2 Page 1 of 1
APPLICATION NO. : 11/137313
DATED : May 8, 2007
INVENTOR(S) : Elliott Richelson and Paul R. Carlier It is certified that error appears in the above-identified patent and that said Letters Patent is hereby corrected as shown below:

Column 20, line 4 (Claim 1), please delete "2'naphthyl" and insert --2'-naphthyl-- therefor;

Column 20, line 6 (Claim 2), please delete "2'naphthyl" and insert --2'-naphthyl-- therefor;

Column 20, line 8 (Claim 2), please delete "2'naphthyl" and insert --2'-naphthyl-- therefor;

Column 20, line 12 (Claim 3), please delete "2'naphthyl" and insert --2'-naphthyl-- therefor;

Column 20, line 14 (Claim 3), please delete "2'naphthyl" and insert --2'-naphthyl-- therefor;

Column 20, line 26 (Claim 4), please delete "2'naphthyl" and insert --2'-naphthyl-- therefor;

Column 20, line 28 (Claim 4), please delete "3hydroxy" and insert --3-hydroxy-- therefor;

Column 20, lines 32-33 (Claim 4), please delete "2'naphthyl" and insert --2'-naphthyl-- therefor;

Column 20, line 34 (Claim 4), please delete "2'naphthyl" and insert --2'-naphthyl-- therefor.

Signed and Sealed this

Thirty-first Day of July, 2007

JON W. DUDAS
*Director of the United States Patent and Trademark Office*